(12) United States Patent
Nakao

(10) Patent No.: US 7,842,046 B1
(45) Date of Patent: Nov. 30, 2010

(54) ENDOSCOPIC SEWING DEVICE AND ASSOCIATED METHOD

(75) Inventor: Naomi L. Nakao, New York, NY (US)

(73) Assignee: Granit Medical Innovations, LLC, New York, NY (US)

( * ) Notice: Subject to any disclaimer, the term of this patent is extended or adjusted under 35 U.S.C. 154(b) by 310 days.

(21) Appl. No.: 11/138,140

(22) Filed: May 26, 2005

Related U.S. Application Data

(60) Provisional application No. 60/574,462, filed on May 26, 2004.

(51) Int. Cl.
*A61B 17/12* (2006.01)

(52) U.S. Cl. .................................................. 606/144

(58) Field of Classification Search ......... 606/144–148, 606/222–227; 604/95.05, 530
See application file for complete search history.

(56) References Cited

U.S. PATENT DOCUMENTS

| | | | |
|---|---|---|---|
| 3,868,956 A * | 3/1975 | Alfidi et al. ................. 606/194 |
| 4,665,906 A | 5/1987 | Jervis | |
| 5,037,433 A | 8/1991 | Wilk et al. | |
| 5,152,769 A * | 10/1992 | Baber ......................... 606/145 |
| 5,499,991 A * | 3/1996 | Garman et al. .............. 606/148 |
| 5,776,148 A * | 7/1998 | Christy ....................... 606/144 |
| 5,820,628 A * | 10/1998 | Middleman et al. ......... 606/147 |
| 7,150,753 B2 * | 12/2006 | Rehil ........................ 606/144 |
| 2007/0135838 A1 * | 6/2007 | Meyer ........................ 606/222 |

\* cited by examiner

*Primary Examiner*—Todd E Manahan
*Assistant Examiner*—Eric Blatt
(74) *Attorney, Agent, or Firm*—R. Neil Sudol; Henry D. Coleman; William J. Sapone

(57) ABSTRACT

A hollow suture needle and related suturing assembly to be used in conjunction with flexible or rigid endoscopy, or on the external surface of the body. The invention relates to performing suturing on internal body tissue as part of a surgical procedure, or on external body tissues. The suturing assembly includes a hollow suture needle which in one preferred embodiment is temperature biased, with associated suturing assembly and an associated method for performing the suturing function.

5 Claims, 22 Drawing Sheets

ENDOSCOPIC SEWING DEVICE AND ASSOCIATED METHOD

CROSS-REFERENCE TO RELATED APPLICATION

This application claims the benefit of the priority of U.S. Provisional Application Ser. No. 60/574,462, filed on May 26, 2004, entitled "Endoscopic Sewing Device and Associated Method," which application is incorporated herein by reference in its entirety.

FIELD OF THE INVENTION

The present invention relates to suturing and, more particularly, to a device or method that works in conjunction with a flexible endoscope to suture tissue within the body, or on its outer surfaces. This invention has particular applicability for suturing in conjunction with an endoscope inside internal body cavities of a patient, for example, inside the abdomen by gaining access through an existing orifice.

BACKGROUND OF THE INVENTION

Surgery in the abdomen is presently performed either through an incision that permits access to the operative site (laparotomy), or via rigid tubes inserted into small incisions in the abdominal wall through which the surgery is performed while being visualized by a camera (laparoscopy). There is no device or method for sewing or stapling through the flexible endoscope. Procedures performed through the flexible endoscope are primarily diagnostic in nature with the exception of biopsy and polypectomy.

There is a large segment of the population that suffers from morbid obesity, which has reached epidemic proportions in the USA. Obesity and its associated health problems have substantial economic consequences for the United States health care system; in 2003, the total costs attributable to obesity were estimated at $70 billion. For selected patients, surgical therapy, referred to as bariatric surgery, is the most effective treatment modality and has been recognized by the National Institutes of Health Consensus Panel as the only successful long-term treatment for morbid obesity. The Roux-en-Y gastric bypass, the procedure most commonly performed, combines a stomach restriction procedure and intestinal bypass, wherein part of the small intestine is stapled to the remaining stomach pouch.

The Roux-en-Y gastric bypass operation achieves successful outcomes in the majority of patients in terms of weight reduction and improvement of co morbid conditions, however it is a long and risky operation. When performed through a large abdominal incision, the procedure requires 2-5 hours of general anesthesia, many days in the hospital, significant use of medication for post operative pain and lengthy periods of convalescence.

Surgical procedures performed on the morbidly obese have a high incidence of complications because of the co morbid conditions that these patients suffer from. Oftentimes the surgeon has to dissect adhesions and free the bowel in order to get to the operative site. This procedure is quite difficult, and has to be performed before the actual bypass and gastric stapling operation has even begun.

When Roux-en-Y bypass surgery is performed laparoscopically, the incisions are smaller, but the abdomen is filled with a large amount of gas in order to distend it and enable the surgeon to perform the operation. The surgery is more difficult and typically takes 1-2 hours longer than the open operation. This requires longer anesthesia time increasing the danger to the patient. The distended abdomen impinges on the patient's lungs decreasing breathing capacity and adding morbidity. While this is a less invasive procedure than open surgery, it still entails significant complications and lengthy patient convalescence. Furthermore, because the surgery takes longer than open surgery, risk to the patient is increased from prolonged general anesthesia.

Providing a flexible suturing method and device to be used in conjunction with a flexible endoscope would significantly reduce the length and complexity of the surgery. Consequently, morbidity and mortality would be decreased, hospital stay shortened, and cost savings provided. Because flexible endoscopic procedures are typically performed under conscious sedation and are much less invasive, they are naturally less traumatic to the body. Convalescence is significantly shortened, postoperative pain is virtually eliminated and patients are ambulatory within hours after an endoscopic procedure.

Although there appear to be no commercial devices that enable suturing through the working channel of a flexible endoscope, U.S. Pat. No. 5,037,433 to Wilk et al. describes an endoscopic suturing device that comprises an endoscope and a needle having a mechanical spring bias construction tending to bend the needle into an arcuate configuration. The needle is disposed in a straightened configuration while inside the endoscope. The surgical instrument further comprises an ejector device in the form of an elongate flexible rod member slidably disposed inside the inner tubular member proximally of the needle for ejecting a needle, which mechanically assumes an arcuate configuration subsequent to its ejection.

Based on the disclosure and drawings of the '433 patent, the mechanical spring biased or elastic tendency of the needle tends to bend a needle in an arcuate configuration. As such, this pre-stressed plastic or metal needle may be deformed (i.e. straightened) by mechanical stresses on the needle being confined in a generally straight biopsy channel of an endoscope, deforming the needle to render it generally straight. The mechanical stresses are provided and maintained by the walls of the biopsy channel into which the needle is inserted. Once the needle is ejected out of the biopsy channel by a rod, the stresses are removed, and the free needle immediately assumes its pre-stressed arcuate configuration under the direction of its normal elastic properties.

The device described in the '433 patent presents various drawbacks and problems. First, the flexible endoscope is constructed in such a fashion as to allow only a 1 cm "stiff length" or less to pass through its biopsy or working channel. Any embodiment with a stiff length longer than 1 cm will not be capable of being passed through the working channel when the endoscope is bent, and will prevent the flexible endoscope from bending when housed inside its working channel. Consequently, only a device that is sufficiently malleable to bend relatively easily along with the endoscope may be passed through its working channel.

Suturing requires a rigid needle shaped in an arcuate form. When such a needle is plunged into the target tissue in one location, it will exit the tissue at a second location in a predictable manner because of the needle's arcuate configuration and stiff or rigid state. Accordingly, there are two important requirements that a suture needle must fulfill if it were to be used through the working channel of a flexible endoscope. On one hand, it must be malleable enough to be passed through the working channel of a flexible endoscope while an endoscope is bent to its maximum capacity, while on the other hand it must assume a rigid arcuate state in readiness for the suturing operation upon ejection. If the spring biased needle described in the '433 patent were to be sufficiently malleable to be passed through the working channel of an endoscope, it would surely be too malleable to enter and exit tissue in a reliable fashion. If a needle were to be formed from a material stiff enough to effectively and consistently enter and exit tissue, it would surely not be malleable enough pass through the working channel of a flexible endoscope.

A further problem that the device described in the '433 patent presents is its lack of anticipation of the difficulty presented in grasping the suture needle with the manipulation device. Just as in open and laparoscopic surgery, a suture needle must be grasped firmly so as not to rotate on its axis during the plunging of a needle into tissue. If the needle is permitted to rotate on its own axis it will only push against the tissue but will not enter it. Grasping a needle with jaw-closure-force being transmitted through a short rigid shaft, as is done during open or laparoscopic surgery is significantly different from grasping a needle with closure force being transmitted through a long flexible shaft. The latter forces required to close the jaws tightly are infinitely greater than in the former case. The '433 patent does not address such an issue. No special construction of the needle's shaft to enhance grasping is described, and the description of the grasping device does not anticipate any of the abovementioned difficulty.

Also, the '433 patent does not address the attachment of the suturing thread to the needle. Spring biased metals do not behave as stainless steel does. In the case of the stainless steel suture needle, the suture thread is inserted into a cavity at the proximal end of the needle and the metal is crimped over the thread. In the case of a needle made of a spring biased metal, the metal is too soft to retain the thread by mere crimping.

Lastly, when operating a needle through an endoscope, it is very difficult, if not impossible, to perform the rotating motion that is required to plunge the needle into the tissue, through the tissue, and out, as performed by the human hand. The simplest motion when working through an endoscope is the push-pull motion.

OBJECTS OF THE INVENTION

A general object of the present invention is to provide a suturing device and/or method that addresses the shortcomings and drawbacks of the prior art.

It is a more specific object of the present invention to provide an instrument assembly for suturing tissues internal to a patient's body by utilizing flexible or rigid endoscopes inserted primarily, though not exclusively, through existing body orifices.

It is a further object of the present invention to provide such an instrument assembly for performing surgery through an endoscope, whereby the instrument assembly may be passed through a narrow, preferably flexible working channel of the endoscope.

A further object of the present invention is to provide a suturing needle that is malleable enough to pass through a working channel of a flexible endoscope without inhibiting the endoscope's bending maneuverability, and yet is rigid for use during a suturing operation.

It is another object of the present invention to provide such a needle that one is able to manipulate by means of a push-pull motion.

It is also desirable to provide an associated method for suturing through an endoscope, supplementing or replacing the more invasive surgical procedures, and reducing the complications and drawbacks of existing open or laparoscopic surgical procedures particularly those performed for morbid obesity.

The benefits of the present invention in addressing the drawbacks and shortcomings of the prior art and the objectives and needs noted above will be more readily apparent from the description and drawings of the invention set forth herein. Although all of the objects of the invention are believed to be attained by at least one embodiment of the invention, there is not necessarily any single embodiment that achieves all of the objects of the invention. Other objects of the invention will be apparent from the drawings and descriptions herein.

SUMMARY OF THE INVENTION

A suturing assembly comprises, in accordance with the present invention, a suture needle having a shaft and a pointed distal tip, a hollow passageway extending longitudinally through the shaft to an opening proximate the tip, and a suture thread slidably extending through the passageway and out of the needle opening.

This suturing assembly, as will be apparent from the drawings and descriptions herein, may be used for closing wounds and incisions on skin and other surfaces external to a patient. The suturing assembly may alternatively be used for closing wounds or incisions in internal body tissues of a patient, for instance, an in endoscopic operation. The assembly may also be used to close diverticulae in the gastrointestinal tract, or for purposes of marking. To that end, the suturing assembly may further comprise an elongate tubular member housing the needle and the suture and a push rod or other means operatively engaging the needle for moving the needle along the tubular member.

The elongate tubular member may be provided with a metal collar proximate a distal end, the metal collar having a lumen with a cross-sectional shape configured to match a cross-sectional shape of the needle. The matching shapes enable a control of the orientation of the needle upon an ejection thereof from the distal end of the tubular member. Where the needle is made of a temperature-sensitive or -responsive shape memory material such as Nitinol, the metal collar may be electrified for purposes of heating the needle and causing it to assume a predetermined configuration conducive to carrying out an endoscopic suturing operation.

An endoscopic suturing assembly for use with an endoscope comprises, in accordance with the present invention, a suture needle, a suture thread, and an elongate tubular member. The suture needle has an elongate flexible shaft that extends substantially the length of an endoscope working channel and a longitudinal passageway extending substantially along the length of the needle, including the shaft, and is made of a shape-memory or spring-biased material tending to form the needle into a predetermined configuration. The needle is sharpened at its distal end and has a distal end portion bent to form a hook or curved configuration assumed by the needle when it is moved out of the tubular member. The long flexible needle is longer than the tubular member so that the needle can be pushed and pulled in and out of the tubular member. The suture thread slidably extends through the passageway in the needle, while the tubular member is configured for passage through a working channel of an endoscope. The needle is slidably positioned inside the elongate tubular member so that the needle can be moved alternately in a distal and a proximal direction. The needle and its shaft may be configured as one continuous tube, i.e., the shaft is integral with or fixed to a distal end portion of the needle so that the distal end portion of the needle is inseparable from the shaft.

The tubular member may include a channel for directing fluid therethrough.

A method for suturing internal body tissues comprises, in accordance with the present invention, the steps of (a) providing a suture needle having a passageway extending substantially along the length of the needle, the needle having a sharp distal tip, (b) providing a suture thread extending substantially through the passageway and out of the needle through an opening proximate the distal tip, and (c) introducing the distal tip with a distal portion of the suture thread exiting through opening into tissue of a patient at a first area and passing it through the patient's tissue. The method further comprises the steps of (d) upon the exit of the needle tip with the suture thread from the tissue, creating a first loop in the distal portion of the suture thread, (e) withdrawing the needle from the patient's tissue, and (f) re-introducing the needle into the patient's tissue at a second area proximate the enlarged loop and repeating steps (d) through (f) above to create a second loop, Further steps of this method include (g) placing the second loop through the first loop, thereby producing a first chain stitch, and (h) re-introducing the needle into the patient's tissue at a third area adjacent to the first chain stitch and repeating steps (d) through (f) above to create a third loop and repeating step (g) to thread the third loop through the second loop, thereby creating a second chain stitch. Additional steps of this method include (i) repeating the process of steps (i), (d) and (e) until a preselected area to be sutured is completely sutured by a multiple-stitch chain stitch, (j) severing the suture thread at a location between the multiple-stitch chain stitch and a remaining portion of the suture thread, and (k) pulling a cut end of the suture thread through a last loop of the multiple-stitch chain stitch, thus creating a knot.

It is to be noted that one may use only two stitches in a chain stich if the defect to be closed is a small one. Moreover, the methodology of the present invention may be useful where only one loop is required, for instance, to close a puncture wound of a certain size. The single loop is formed and then knotted to form a suture.

As indicated above, this method may be used on external (e.g., skin) tissues, or on internal body tissues in an endoscopic (rigid or flexible) operation. Where the endoscope is a flexible endoscope, the needle is preferably made of a shape memory metal or a spring biased material. In that case the method also comprises housing the needle in a first configuration inside the working channel of the endoscope and ejecting the needle from a distal end of the working channel, the needle assuming a predetermined configuration upon ejection from the working channel.

A medical method comprises, in accordance with another embodiment of the present invention, (i) inserting a hollow needle through an entrance point a patient's skin above a jaw of the patient, the needle having a suture thread extending longitudinally through the needle, (ii) moving the inserted needle along a first path down the patient's jaw and into a fat pad or tissue that is sagging with purpose of tightening said tissue to an exit point at a lower portion of the jaw, (iii) removing the needle from the patient through the exit point, (iv) reinserting the hollow needle into the patient's jaw through the exit point, (v) moving the reinserted needle, with the thread extending therethough, along a second path upwardly along the patient's jaw to the entrance point, the second path being different from the first path, (vi) removing the reinserted needle from the patient through the entrance point, (vii) pulling on the suture thread at the entrance point to tighten jaw tissues, and (viii) coupling opposing ends of the thread to one another to form a closed loop in the patient's jaw.

In accordance with the present invention, there is provided a device and a method for intracorporeal sewing through a flexible endoscope. This device includes a hollow suturing needle made of a Shape Memory Alloy. The needle has a longitudinal channel or passageway that is traversed by a suture thread or another flexible line. The device further includes a needle delivery and deployment component. The method of the present invention entails a particular procedure for suturing. This device may be used in conjunction with a flexible or rigid endoscope, or during sewing outside the body without the use of an endoscope.

In one embodiment of the present invention, the suture needle is made of the temperature biased shape memory alloy Nitinol (NiTi). The Nitinol alloy needle takes on a desired arcuate shape and stiffness appropriate for suturing when the alloy material is heated to a predetermined temperature. When cooled below a specific temperature, the alloy material in turn assumes a malleable state. The ability of the suture needle to return to the previously defined shape when subjected to an appropriate thermal procedure is the basis upon which several embodiments of the temperature biased suture needle function.

Accordingly, the temperature at which the suture needle will be in a heated state may vary. For example, in one embodiment, the suture needle is in a heated state at a temperature proximate body temperature. In another embodiment, the suture needle is in a heated state at a temperature above body temperature.

DETAILED DESCRIPTION OF EMBODIMENTS OF THE INVENTION

Figure 1:
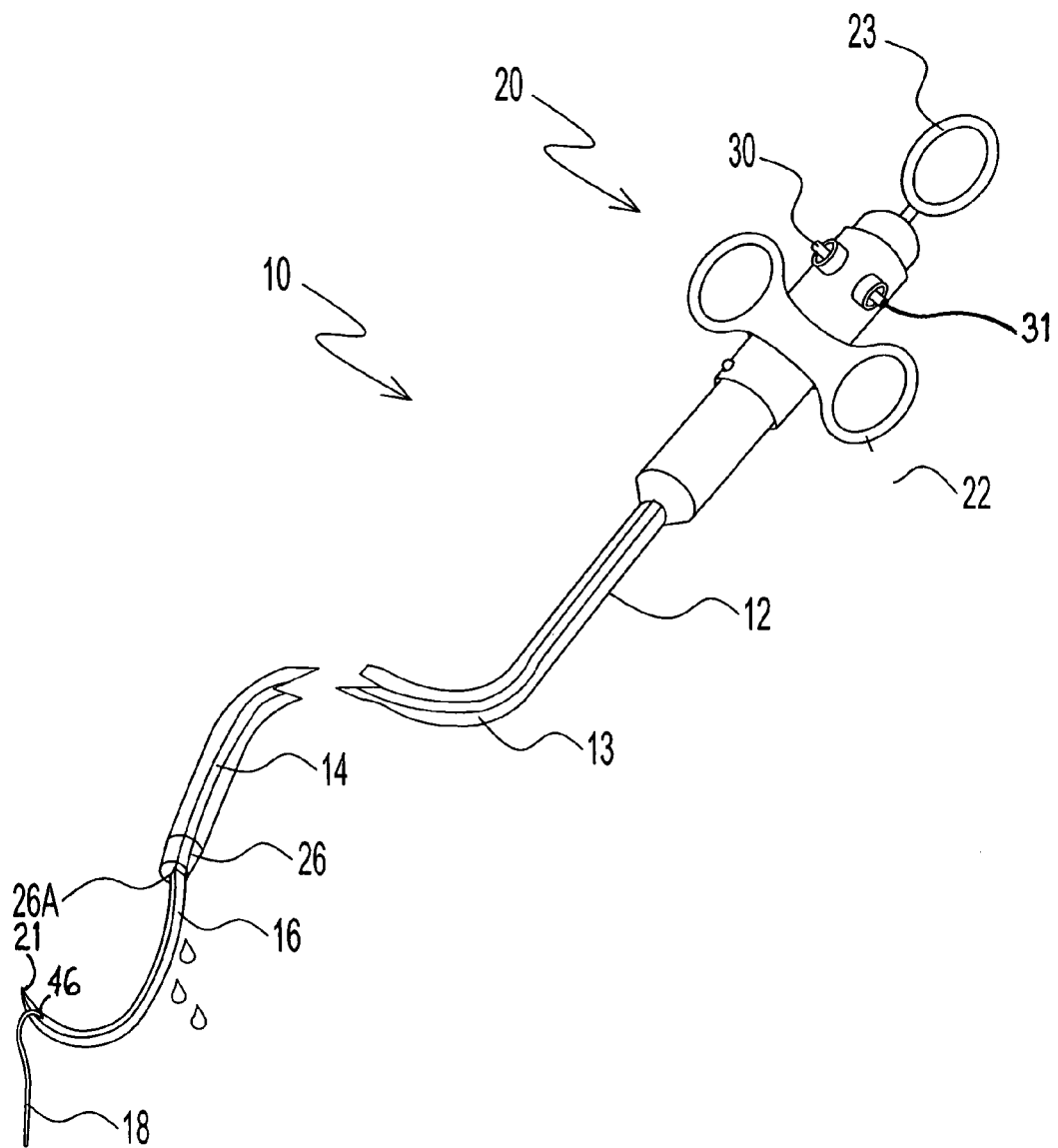
FIG. 1 is a schematic perspective view of an embodiment of an endoscopic suturing device in accordance with the invention.
Figure 2:
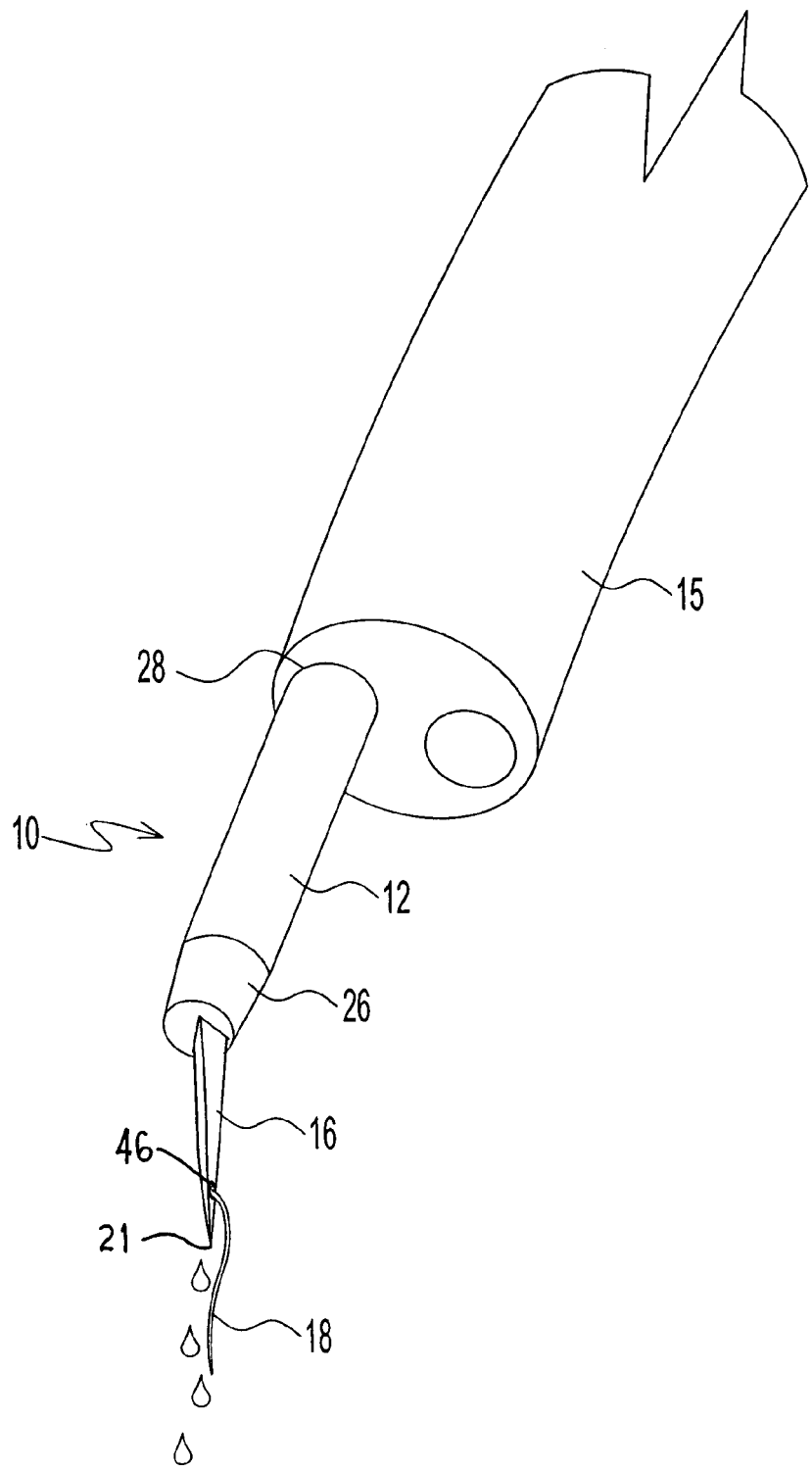
FIG. 2 is a schematic perspective view, on an enlarged scale, of a distal end of the endoscopic suturing device of FIG. 1.

An endoscopic sewing device 10 as illustrated in FIG. 1 is configured for use in a flexible endoscope 15 (FIG. 2). The endoscopic sewing device 10 includes an elongated tubular member or catheter 12 that is insertable into and movable along a working channel 28 of endoscope 15 (see FIG. 2) for positioning and manipulating a hollow suture needle 16. The tubular member 12 is formed of a suitably flexible material.

Needle 16 has an elongate shaft 14 at least partially contained in and movable in a longitudinal direction along the tubular member 12. Shaft 14 is also formed of a suitably flexible material.

Needle 16 comprises a hollow shaft (not separately enumerated) terminating in a sharp distal tip 21. A suture thread 18 passes longitudinally through needle 16 and emerges from an aperture or opening 46 located in a distal end portion of the needle, proximately to distal tip 21. Suture thread 18 may pass longitudinally through shaft 14, as well. Alternatively, suture thread 18 may extend through tubular member 12, outside of shaft 14 and enter needle 16 at a proximal end thereof. In a preferred embodiment, the suture needle 16 is a single elongate flexible tube through which the suture thread 18 slidably passes.

The needle 16 is deployed from the distal end of the tubular member 12 as shown in FIG. 1. The needle 16 is moved via its elongate shaft 14, which is operably coupled to a control system that may include an actuation assembly or handle 20 with a finger ring 22 and a thumb ring 23. The actuation handle 20 is also coupled to the tubular member 12. As shown in FIG. 2, needle 16 is configured in a triangular or rectangular shape. Tubular member 12 is provided at its distal end with a metal collar 26 having an internal lumen 26A configured in the same shape as the needle 16 in order to provide for a snug fit and directional stability of needle 16 within collar 26. Thus, when the distal end of tubular member 12 is positioned proximal a surgical site and needle 16 is ejected, the matching cross-sectional shapes of the needle 16 and the lumen 26A of collar 26 enables one to maintain and control the position and orientation of needle 16 as it enters, traverses, and exits the target tissue, and does not rotate about its axis.

Needle 16 may have various different configurations depending on its use in a particular application. The needle 16 may have a curved, hooked or straight use configuration, which is automatically assumed upon an ejection of the needle from tubular member 12 via collar 26. The needle 16 may be formed from a Shape Memory Alloy (SMA) having a malleable mode at a lower temperature and a more rigid mode at a higher temperature.

Tools made of Shape Memory Alloys (SMA) have the ability to return to a predefined shape or size when the SMA material is subjected to an appropriate thermal energy after an initial deformation in a martensitic (malleable) phase. These SMA materials can be deformed at a relatively low temperature and, upon exposure to a higher temperature, will return to the original shape that was present prior to deformation.

Needle 16 may be particularly made of the SMA material Nitinol (NiTi). Nitinol alloys are most commonly known for their superelasticity and thermal shape memory. The martensite state of a Nitinol material is the low temperature phase wherein the material is malleable, easily deformed to several percent strain at quite a low stress. The austenite phase of the Nitinol material is the high temperature phase wherein the material is hardened.

Devices with components made of Nitinol possess specific transition temperatures. The transition temperature represents the temperature range in which the alloy transforms from a martensite to an austenite state, and vice versa. During the transition period the alloy is in between the two states, and will have proportionately some of the properties of both conditions. The temperature that begins the transition period from martensite to austenite may be represented by the symbol $A_s$ where the letter s stands for "start", and the temperature that ends the transition from martensite to austenite may be represented by $A_f$, where the letter f stands for "finish". Concomitantly, the temperature that begins the transition period from austenite to martensite may be represented by the symbol $M_s$ where the letter s stands for "start", and the temperature that ends the transition from austenite to martensite may be represented by $M_f$, where f is for "finish".

In one embodiment of an endoscopic sewing device, the material of needle 16 has an austenite start temperature $(A_s)$ in the range of 30° C. and an austenite finish temperature $(A_f)$ is in the range of 39° C. Thus, although water with a temperature greater than body temperature will quickly transform the needle to its hardened state, when the needle returns to body temperature it will remain in this hardened state. This is due to the fact that there is a hysteresis associated with the transformation. Hysteresis requires that the alloy be cooled below the $A_s$ and $A_f$ temperature range in order to once again form martensite, the softer state.

Nitinol alloys can be blended very specifically to achieve desired transformation temperatures. The factor that dictates transition temperatures and hysteresis is the proportion of nickel to titanium. This ratio may initially be established by the alloy melter with the intent of achieving a specific transformation temperature range. However, to confirm the desired results, rather than relying on chemical composition, the transformation temperatures may be measured using Differential Scanning Calorimetry (DSC).

Accordingly, in the above-discussed embodiment, the Ni to Ti ratio is such that the austenite start temperature $(A_s)$ is in the range of 30° C. and its austenite finish temperature $(A_f)$ is in the range of 39° C. In another embodiment, the needle assumes its austenitic state at a temperature proximate body temperature. In still another embodiment, the needle assumes its austenitic state at a temperature above body temperature.

As described in U.S. Pat. No. 4,665,906 to Jervis, many shape memory alloys (SMAs) are known to display stress-induced martensite (SIM). When an SMA sample exhibiting stress-induced martensite is stressed at a temperature above $M_f$, the sample first deforms elastically and then, at a critical stress point, begins the formation of stress-induced martensite. Depending on whether the temperature is above or below $A_s$, the behavior when the deforming stress is released differs. If the temperature is below $A_s$, the stress induced martensite is stable; but if the temperature is above $A_s$, the martensite is unstable and transforms back to austenite, with the sample returning to its original predetermined shape. Therefore, when needle 16 requires withdrawal, it may be pulled back into tubular member 12 with minimal or no cooling and become more malleable because of its SIM properties. When needle 16 is ejected again for the next stitch, the material will transform back to austenite so that needle 16 assumes its arcuate, hardened state appropriate for sewing.

The suture thread 18 is flexible and biocompatible. It is capable of being tied and would be available in different thicknesses. The suture thread may be bioabsorbable or non-bioabsorbable.

The metal collar 26 at the distal end of tubular member 12 serves to protect the suture needle tip 21 during insertion of the suturing assembly through the working channel 28 of endoscope 15. Metal collar 26 can also be used to conduct heat to the suture needle 16 to activate the shape memory of the Nitinol material and induce suture needle 16 to assume its predetermined curved configuration when the needle is to be deployed. For example, the needle 16 may start out in a flexible and generally straight shape to fit into the tubular member 12 to be moved through the flexible endoscope's working channel 28. Upon ejection from the distal end of tubular member 12, the needle 16 may be temperature deformed to assume the hook or curved configuration as shown in FIG. 1. To that end, collar 26 may be coupled to a temperature control system (not illustrated) through an electrical connector or port 30 on actuation handle 20. Wires or other conductors (not shown) conduct electrical current to the collar 26 from the port 30 to thereby heat the collar. The collar then transfers the heat to suture needle 16. The collar 26 may be made of a high resistance metal which heats up when current is conducted thereto. Alternatively or additionally, fluid may be used to introduce a temperature change (whether hot or cold) to the needle 16 for the purposes of inducing a shape change. To that end, the tubular member or catheter 12 is provided with a hollow lumen or channel 13 for directing a fluid from a fluid inlet port 31 to suture needle 16. The port 31 may be connectable to a standard fluid injection syringe (not shown), which is the source of temperature specific fluid. In the device 10, the distal end portion of suture needle 16 is forced out of the tubular member 12 proximate a surgical site by pushing needle shaft or rod 14 and may take a straightened configuration as shown in FIG. 2. Heat may then be applied to induce the needle 16 to assume a curved shape for suturing as shown in FIG. 1. If the needle 16 is made of a semi-rigid spring-biased material, it will regain its curved shape when extruded from tubular member 12.

FIG. 2 is a perspective view of the distal end of endoscope 15 with endoscopic sewing device 10 emerging from the working channel 28 of the endoscope. Tubular member 12 with metal collar 26, needle 16 and thread 18 are shown in the pre-heating configuration discussed above.

Figure 3:
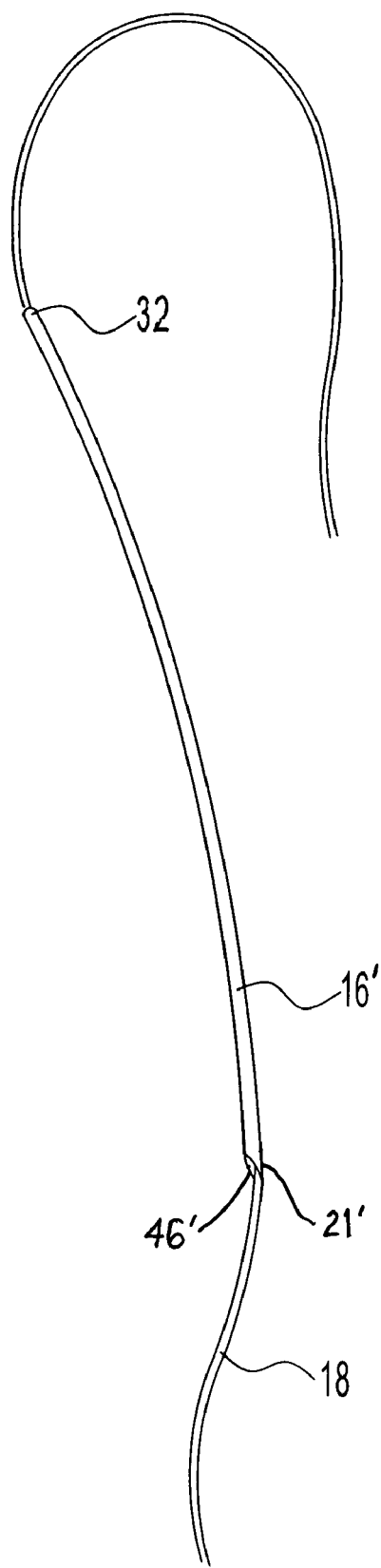
FIG. 3 is a schematic perspective view of a suturing needle in accordance with the present invention.

FIG. 3 illustrates a modified embodiment of a needle 16' wherein thread or suture 18 longitudinally traverses the needle and exits from an opening or aperture 46' at or near a sharp distal end 21' of the needle. The needle 16' has a hollow body so that the thread 18 passes therethrough along its length and specifically passes from a proximal end 32, which is coupled with the push rod 14, to distal end 21' which is sharpened or pointed to penetrate tissue.

A method utilizing device 10 includes introducing the needle tip 21 or 21' with thread 18 exiting proximate the needle tip into tissue 40 (FIG. 4A) and passing the needle 16 or 16' through the tissue by pushing the actuation handle 20 and thereby the push rod 14 connected to the needle 16. When the needle tip 21 or 21' with the thread 18 exits the tissue, a portion of thread 18 is formed into a loop 48 (FIG. 4D). This loop 48 is grasped by a grasper 50 (FIG. 4D) or other flexible device that has a hook 51 at its distal end. A distal end portion of grasper device 50 exits through a separate channel (not shown) of the endoscope 15 and pulls the thread 18, sliding or drawing it through needle 16 and out through aperture 46, to enlarge loop 48. The needle 16 is then withdrawn into the flexible tubular member or catheter 16, leaving a loop of thread 18 in the tissue. The needle 16 may be transformed into its malleable, or martensitic state by washing it with cold water injected through a second working channel the endoscope 15. However, more conveniently, the SIM properties of the SMA material may be utilized, causing the needle 16 to become more malleable by the sheer action of retracting the needle back into the tubular member 12 through lumen 26A of collar 26. The elongated needle could also be made of spring biased Nitinol, or spring biased stainless steel, so that temperature variation is not necessary.

The needle 16 is re-introduced at an adjacent spot to the loop of thread 48, and the above process is repeated, creating two adjacent loops 48 and 54 (see FIGS. 4G through 4K). The second loop 54 is threaded through the first loop 48 by needle 16 and is pulled by hook 51 of grasper or pulling tool 50, thereby producing a first stitch. The needle 16 is then reintroduced at a place adjacent to the second loop 54, and another loop 56 (FIGS. 4F through 4N) is created, which is threaded through the second loop 54 and pulled, thereby creating a second stitch. This process is continued until the entire wound or incision 42 (FIG. 4A) to be sutured is completed.

At this point an endoscopic scissor or other cutter 60 (FIG. 4N) is introduced through another channel of the endoscope 15 and used to cut off the remaining suture material. The cut end 61 of suture thread 18 (FIGS. 4N and 4O) is pulled through the last loop of thread, creating a knot 62 (FIG. 4O).

The sewing process discussed above is implemented by a back and forth motion of the needle 16, which never completely exits the tubular member 12 because the needle is integrally coupled with the push rod 14. This method of sewing is advantageous because the needle 16 is introduced into tissue by actuation and withdrawal of the proximal actuation assembly 20.

The present sewing process is a simple push-pull technique not the usual complex circular motion used in sewing. This method is important because sewing through a flexible endoscope 15 is quite remote and therefore difficult to control. A push-pull motion is the easiest way to handle procedures through the long and flexible shaft of the endoscope 15.

A hollow needle with a longitudinal channel or passageway as described herein can be used as a simple rigid needle with a suture thread extending through the channel or passageway, not through an endoscope, but rather on an external body surface such as a patient's skin. Use of such a needle would be appropriate in children and animals, where suture removal is a problem. This particular stitch enables the removal of the entire length of stitches by one pull on the thread, and the whole length of stitches unravels.

Figure 4A:
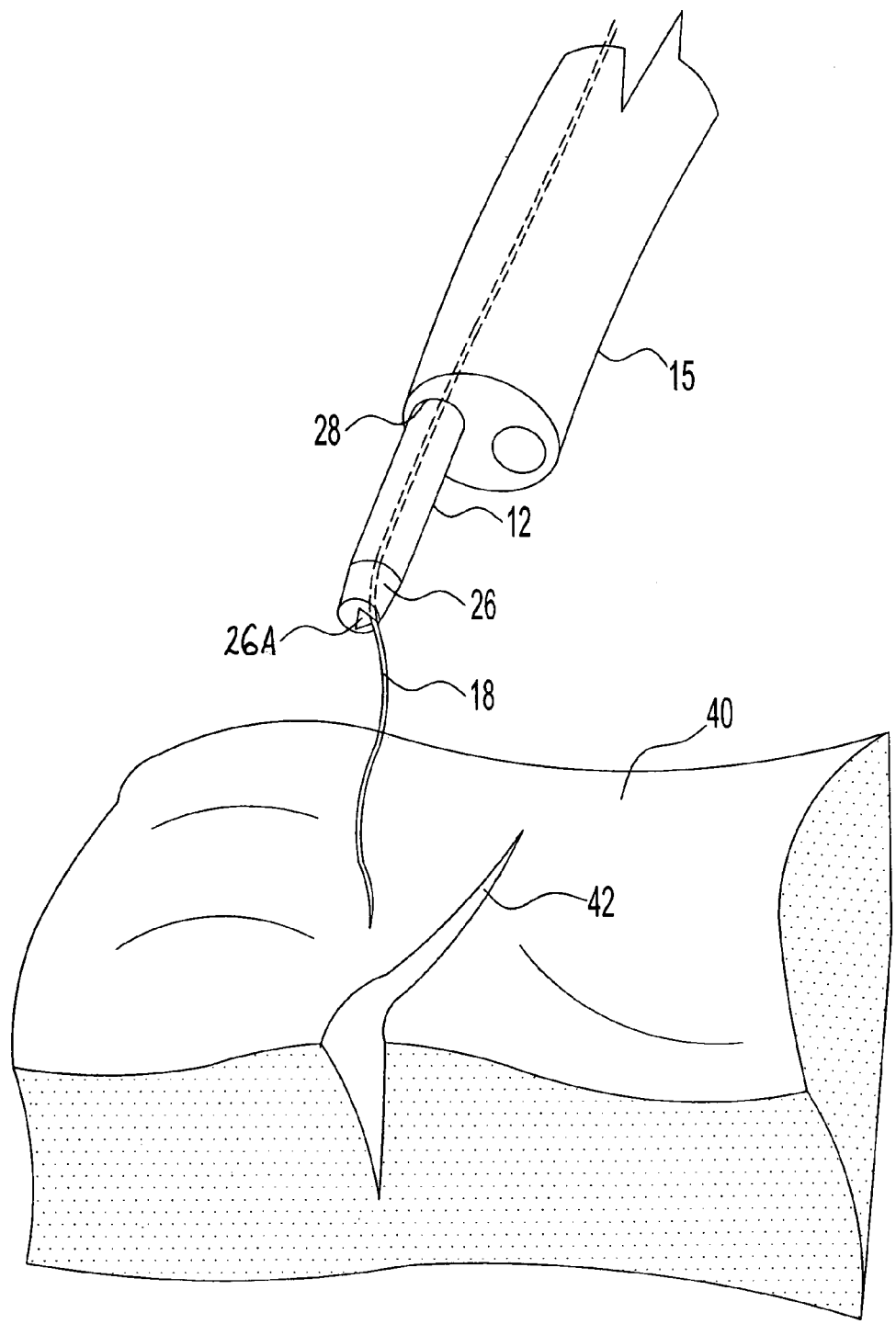
FIGS. 4A-4O are sequential schematic perspective views of the endoscopic suturing device and needle of FIGS. 1-3, showing successive steps in a tissue suturing operation in accordance with the present invention.

FIGS. 4A-4O illustrate the use of the endoscopic suturing device 10 for suturing tissue. As shown in FIG. 4A, endoscope 15 is positioned proximate tissue 40 and specifically proximate wound or incision 42 to be sutured. Tubular member 12 extends through working channel 28 of endoscope 15. Suture thread 18, which is coupled to and traverses needle 16, passes through lumen 26A formed in collar 26 through which the needle passes.

Figure 4B:
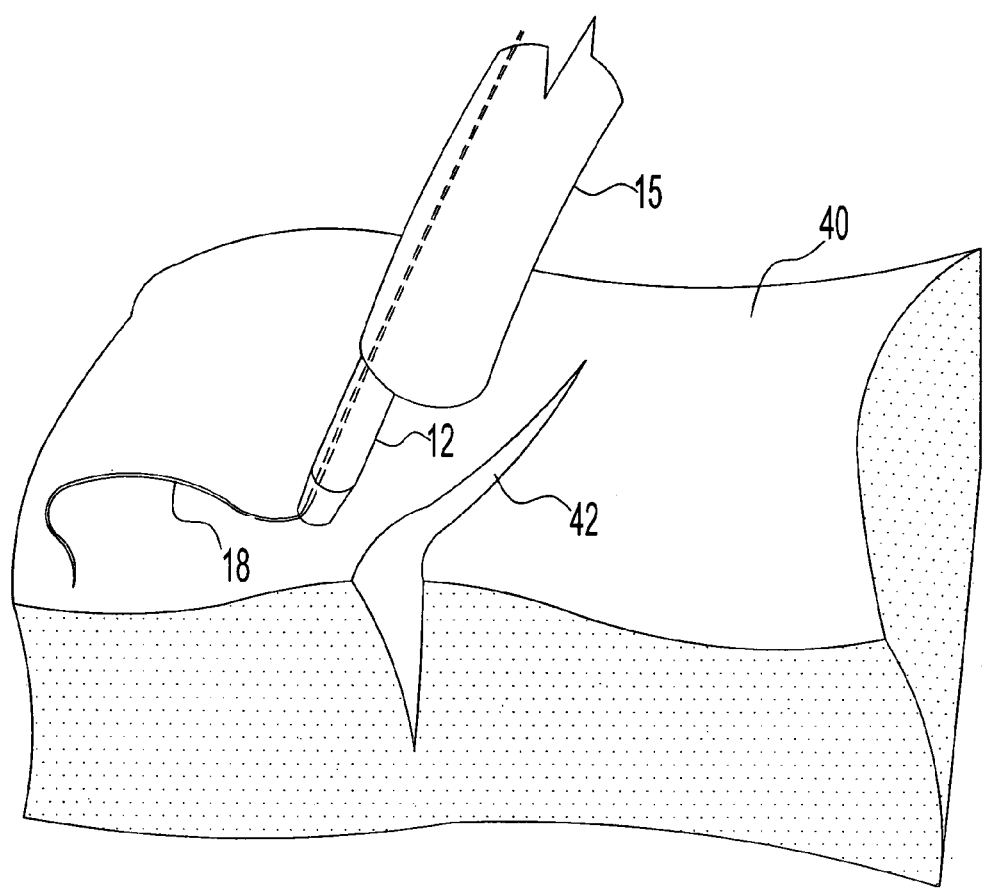
Figure 4C:
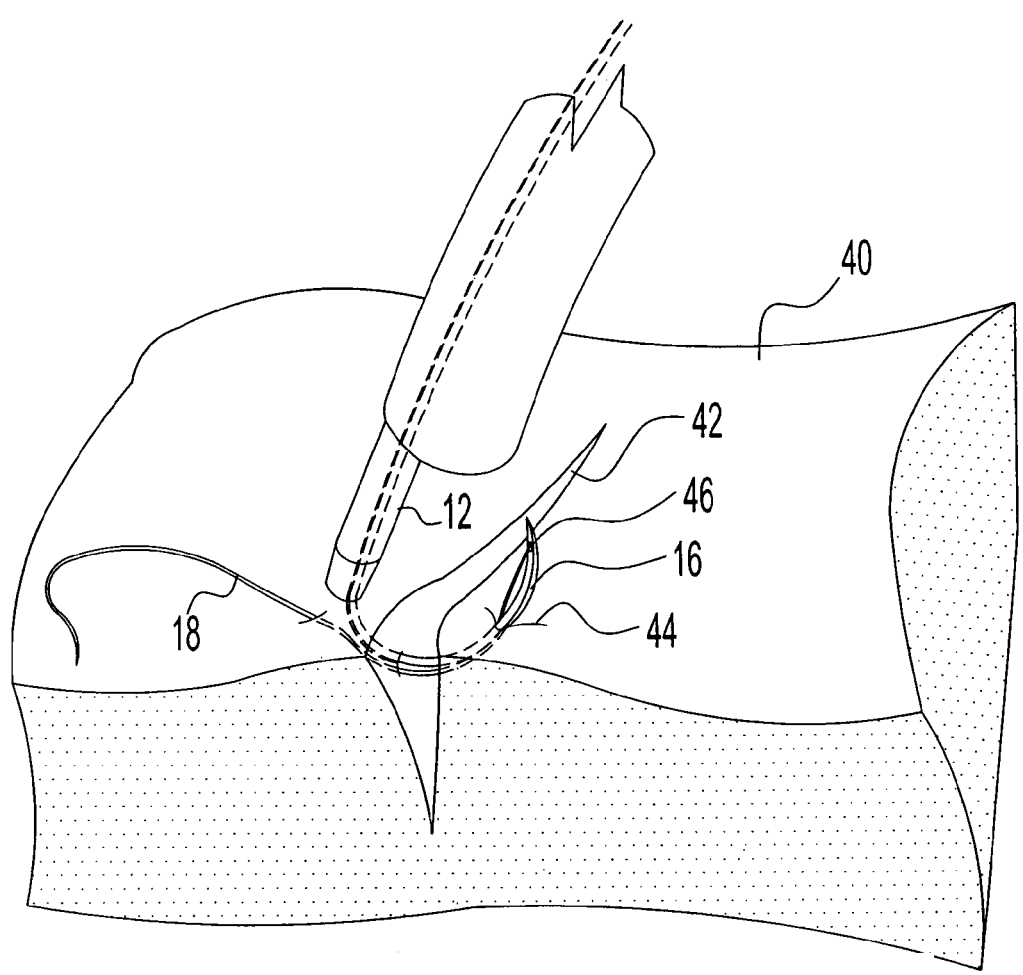
Figure 4D:
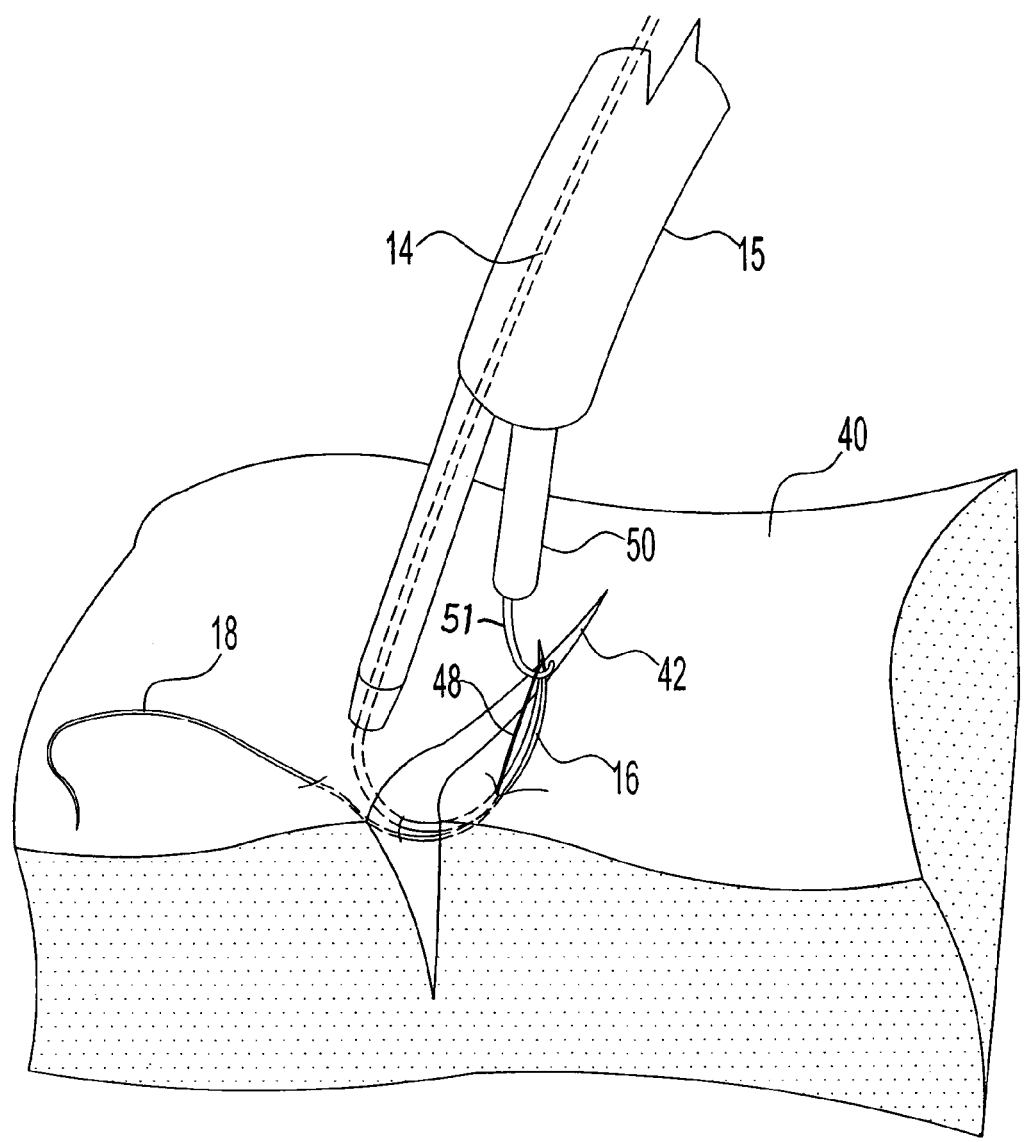

As illustrated in FIG. 4B, the end of tubular member 12 from which the needle 16 is pushed is positioned proximate to the incision 42. As shown in FIG. 4C, the needle 16 is ejected from tubular member 12 and directed through the tissue 40 proximate the incision 42. The needle 16 assumes a curved configuration during insertion through the tissue 40. The assumption of the curved configuration may be the result of an inherent spring bias or temperature deformation, as discussed above. Needle 16 passes through tissue 40 on both sides of the incision 42 and emerges at point 44. The thread 18, which transverses a portion of needle 16 and exists at aperture 46 proximate the distal end 21 of the needle, also passes through the tissue along with the needle.

With reference to FIG. 4D, loop 48 is formed by the needle 16 and the thread 18. Through another working channel (not shown) of endoscope 15, hook 51 of grasper or pulling tool 50 is used to engage the loop 48.

Figure 4E:
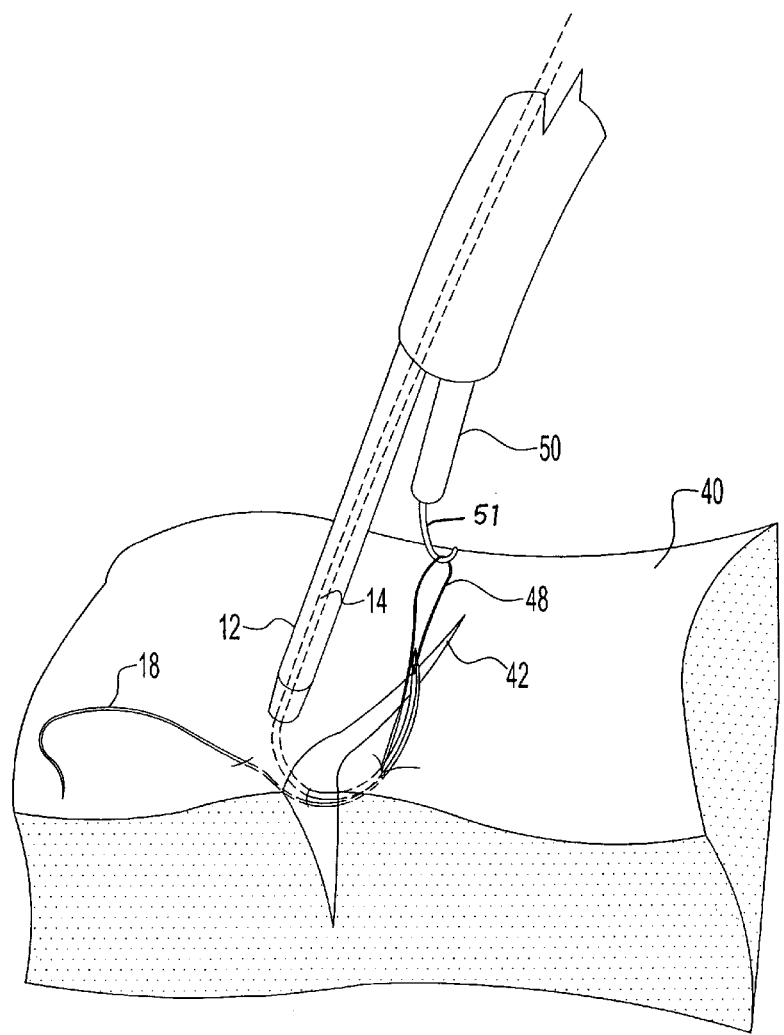
Figure 4F:
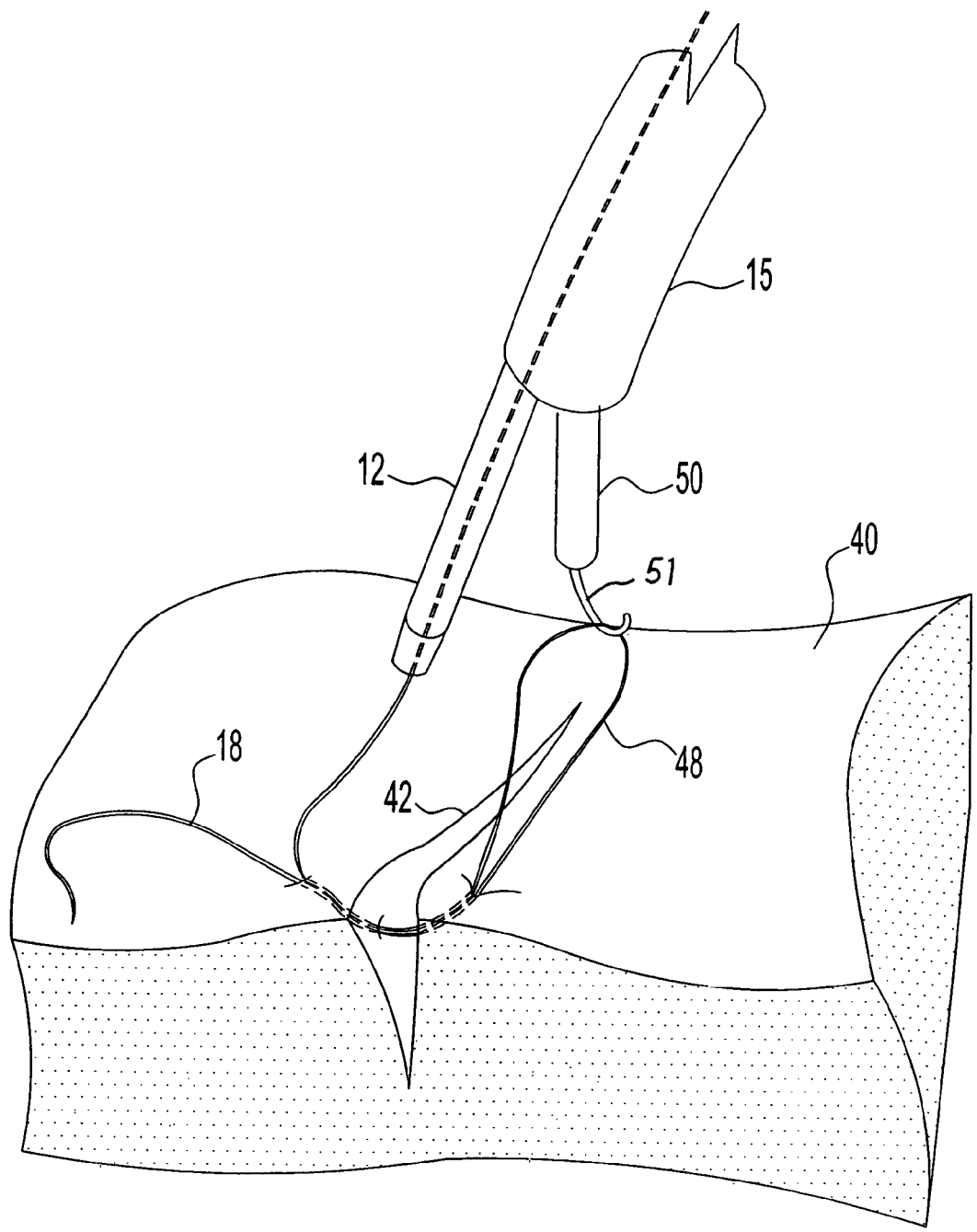

As illustrated in FIG. 4E, the grasper 50 holds the loop 48 proximate one side of the incision 42 while the needle 16 is pulled back across the incision, as illustrated in FIG. 4F. As shown in FIG. 4F, the needle may be retracted into tubular member 12. The retracting or withdrawing of the suture needle 16 back through the patient's tissue includes sliding the needle along a portion of the thread 18 extending from a proximal end 32 of the needle. Alternatively, a portion of needle 16 and a portion of the thread 18 might be left extending out of tubular member 12.

Figure 4G:
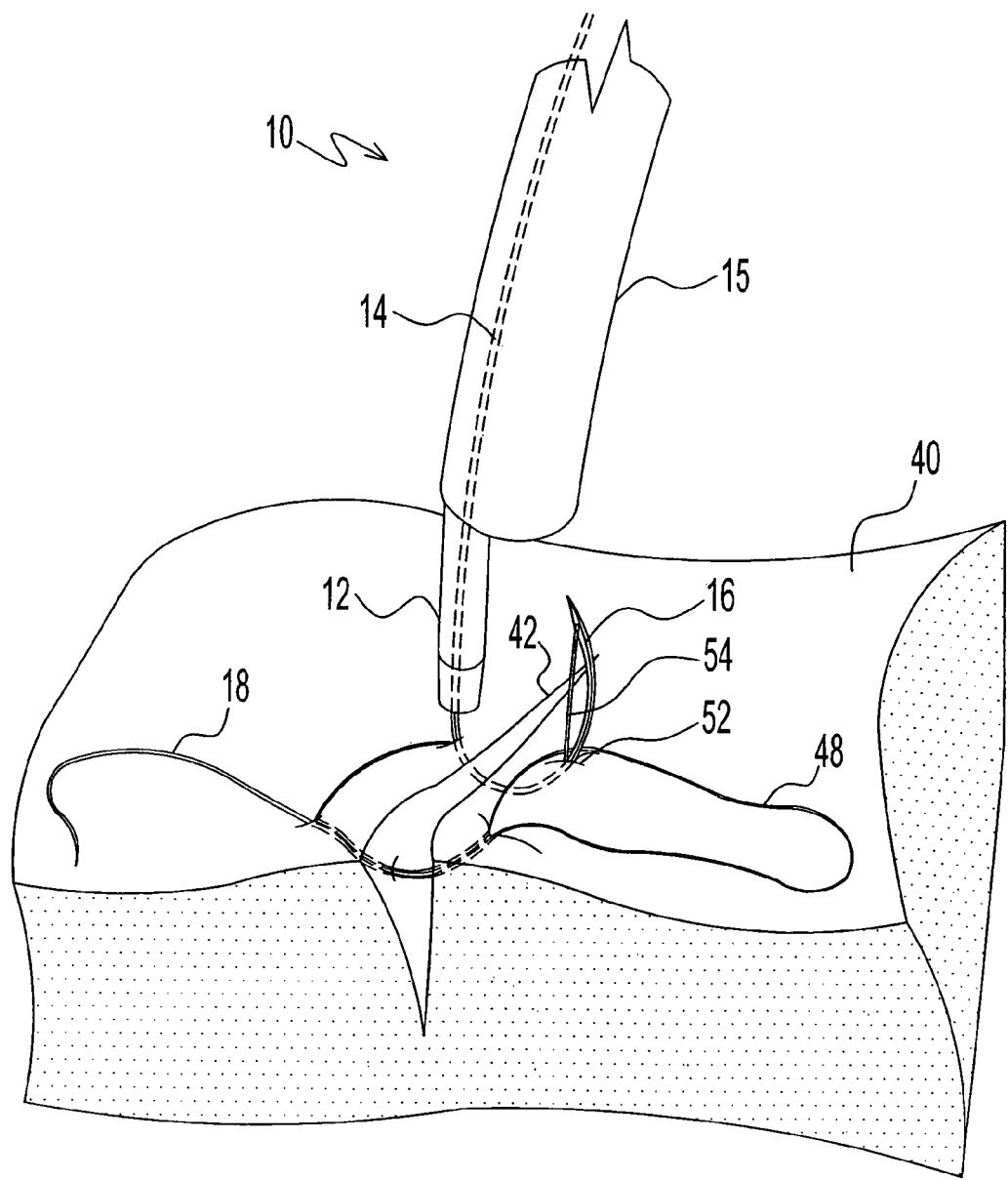

With reference now to FIG. 4G, the device 10, and particularly the end of tubular member 12, is moved to another position further along the longitudinal axis of incision 42. However, the first loop 48 remains proximate the first needle incision position as illustrated. Enough thread 18 has been pulled out by the grasper 50 to make an adequately sized loop 48. The needle 16 is then again inserted into tissue 40 on one side of incision 42, directed across the incision, and ejected out of another tissue exit point 52 on the other side of the incision 42 proximate to loop 48. Preferably, the distal end of the needle 16 is directed through the loop 48.

Figure 4H:
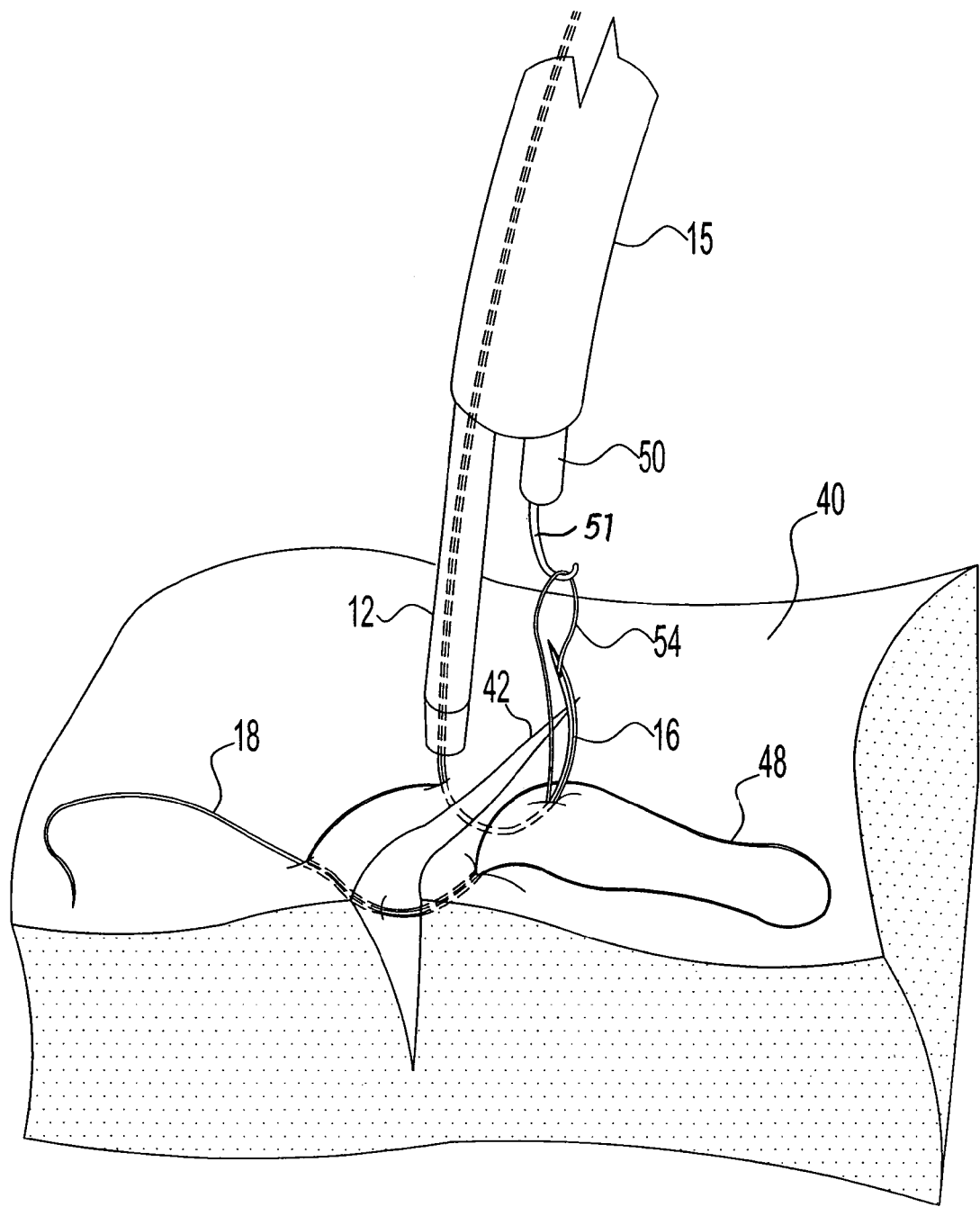
Figure 41:
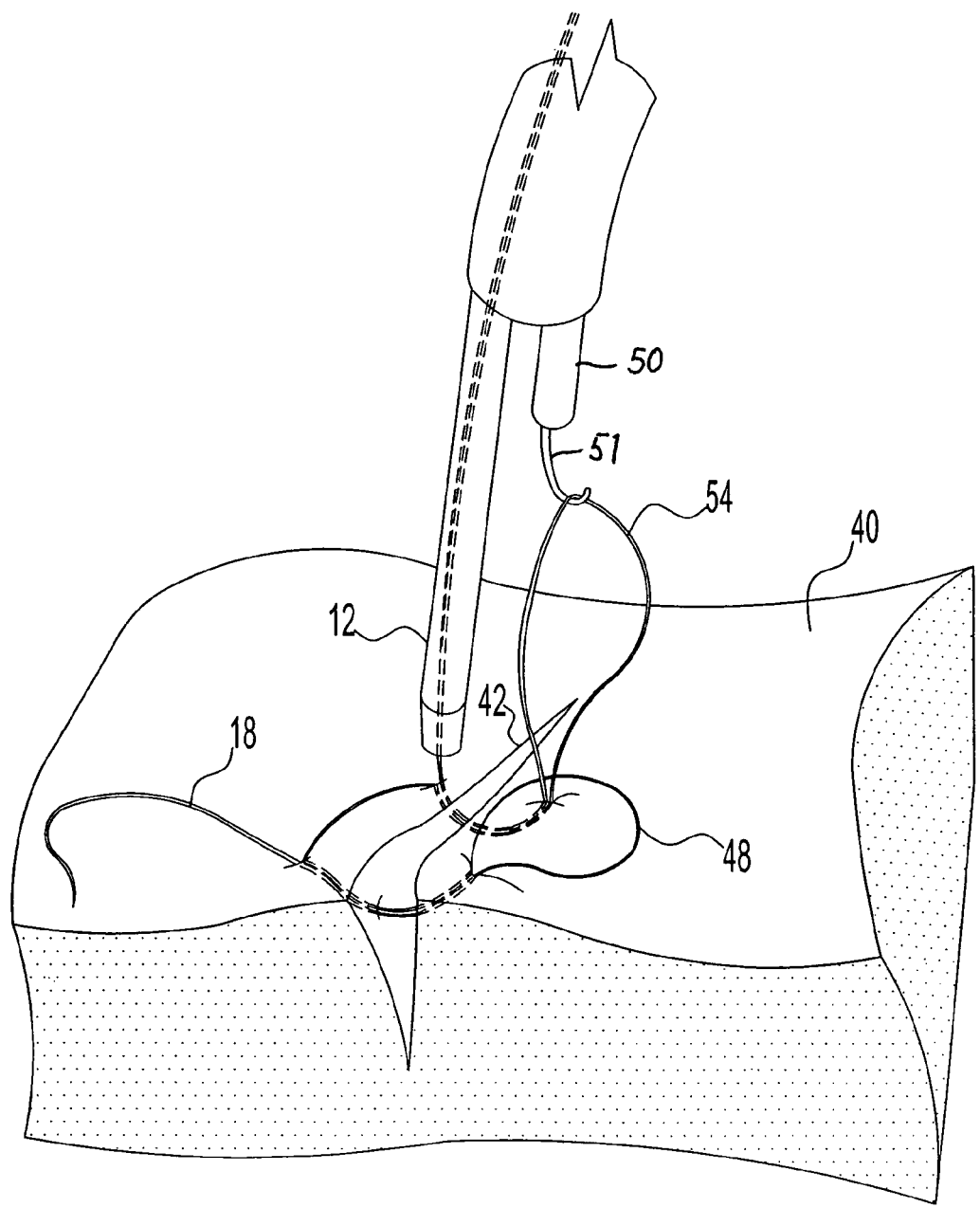
Figure 4J:
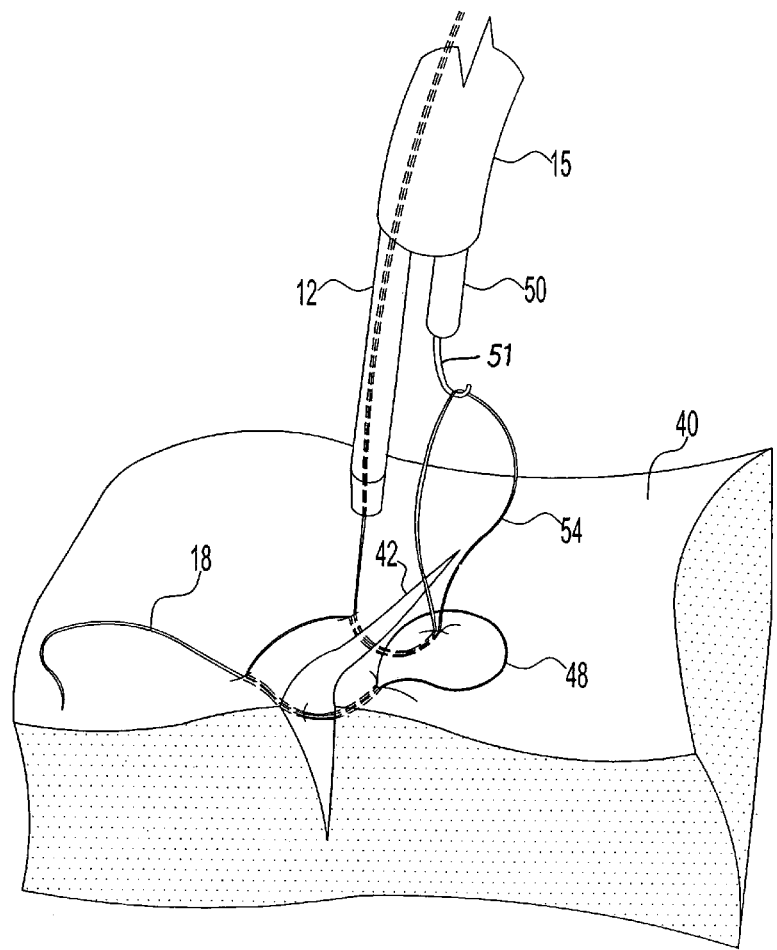

The curved shape assumed by the needle 16 upon its ejection from tubular member 12 and its insertion into tissue 40 allows for entry on one side of the incision 42 and exit on the other side of the incision simply by pushing the needle out of the tubular member 12 via the push rod 14. Needle 16 forms second loop 54 that is then hooked by the grasper 50 as illustrated in FIG. 4H. The needle 16 is then retracted back across the incision 42 as illustrated in FIG. 4I. Loop 54 remains in position on the other side of incision 42 opposite tubular member 12 and extends up loop 48 as illustrated in FIG. 4J.

Figure 4K:
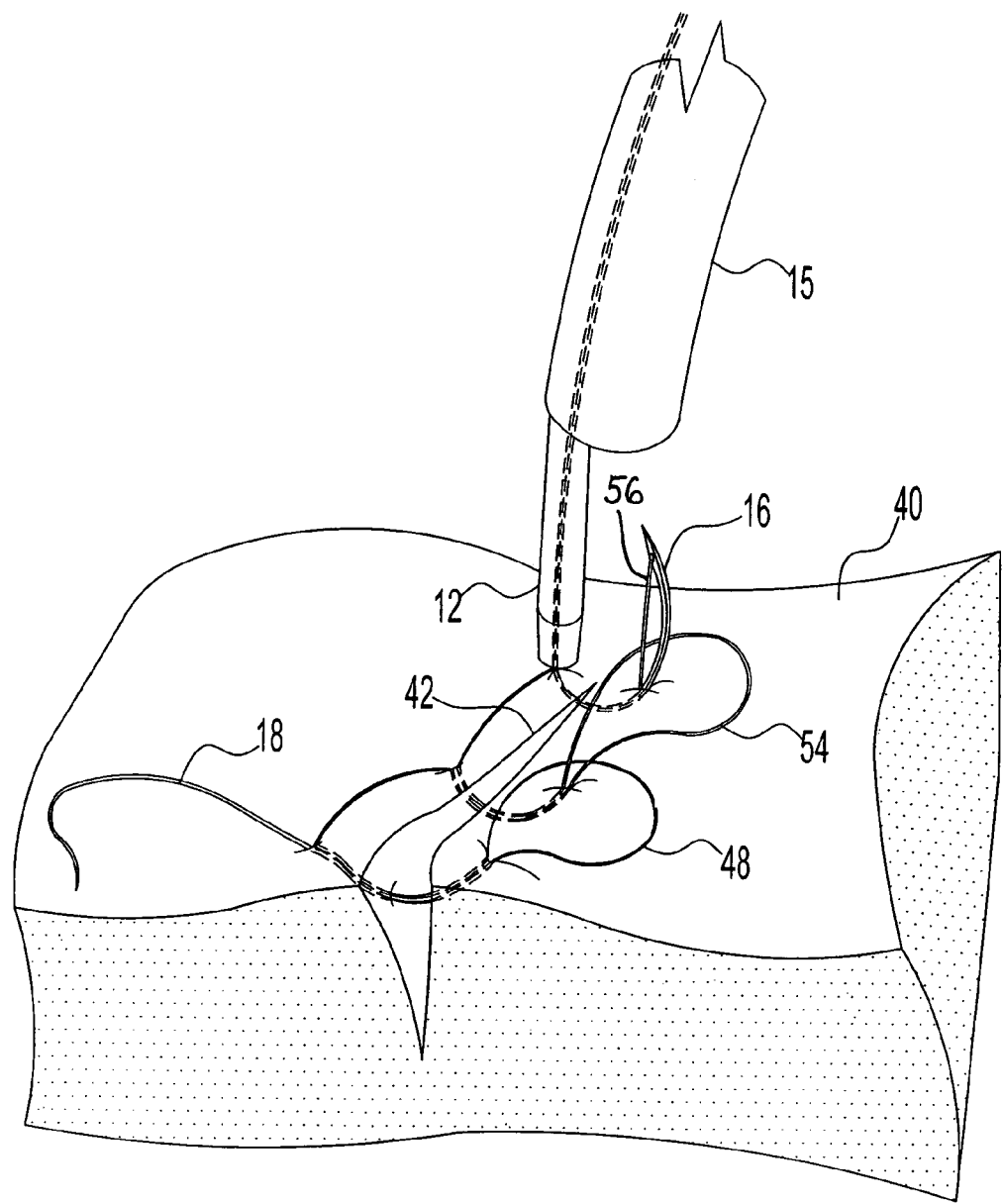
Figure 4L:
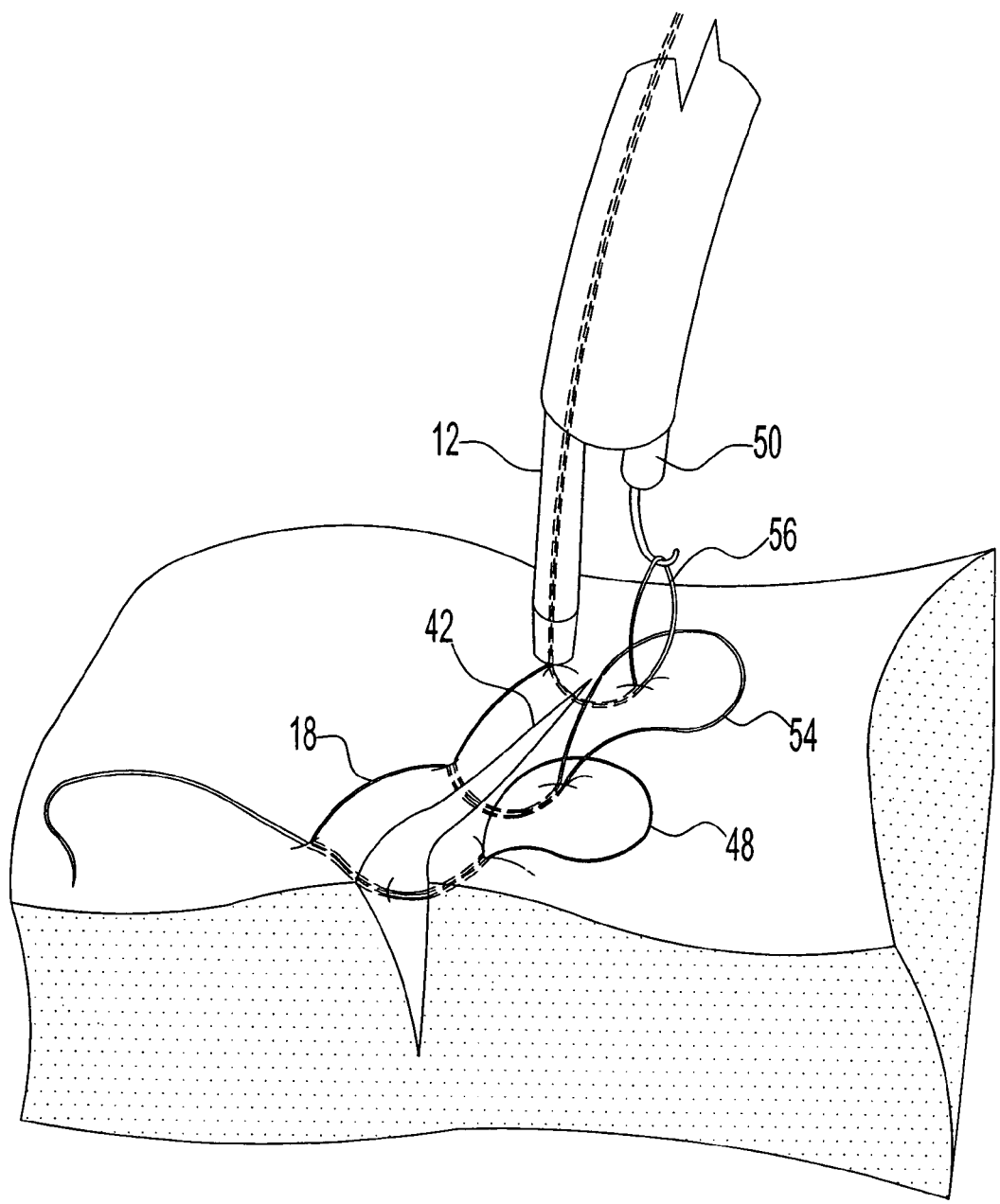

Tubular member 12 and needle 16 are then moved further longitudinally down the incision 42 and the stitching process is repeated as illustrated in FIGS. 4K and 4L. Third loop 56 is formed to extend through the second loop 54. FIG. 4L shows three loops 48, 54, and 56 interconnected to one another in a chain stitch array. Each loop 48, 54, 56 forms a single chain stitch of a concatenated array.

Figure 4M:
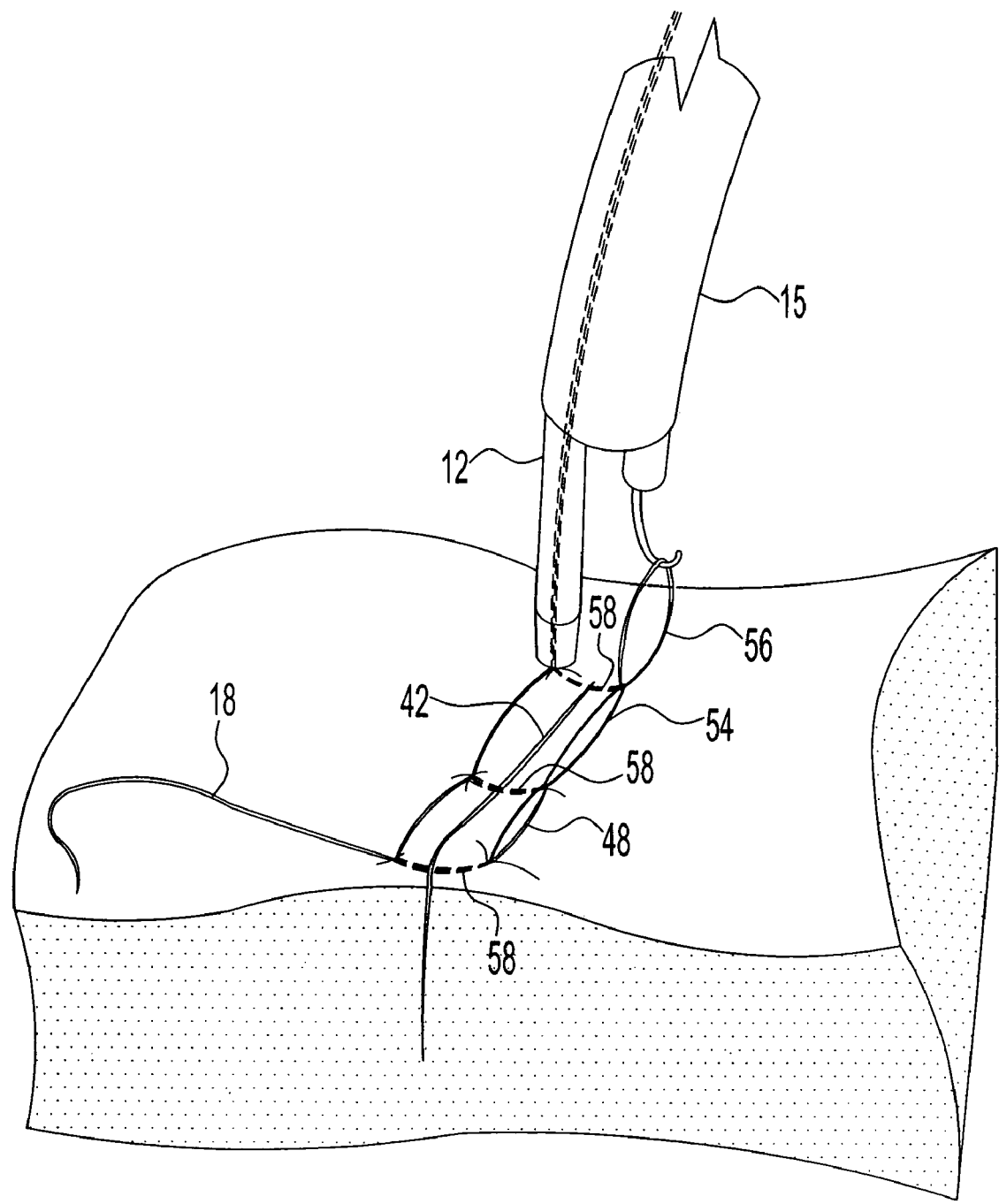
Figure 4N:
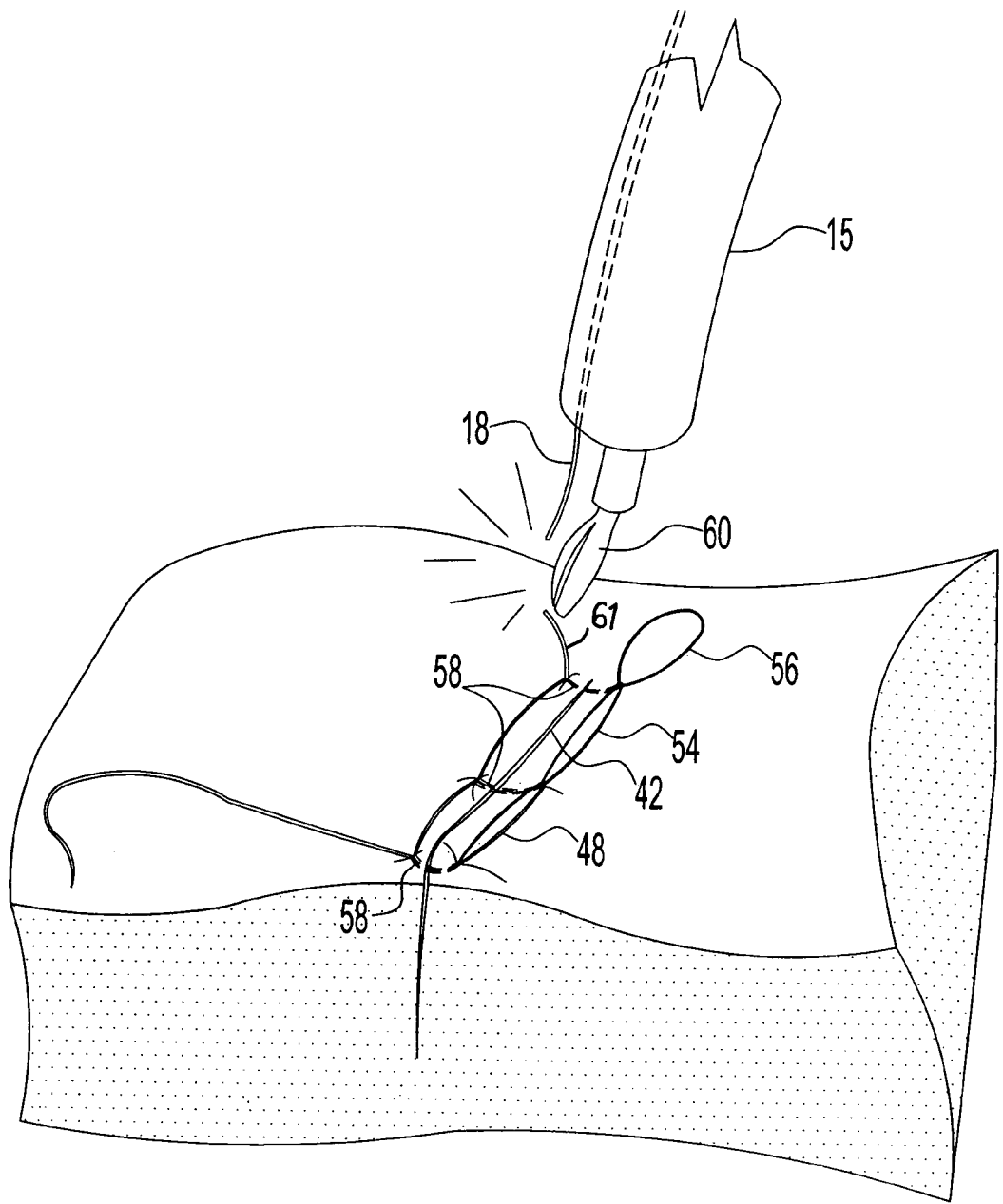
Figure 40:
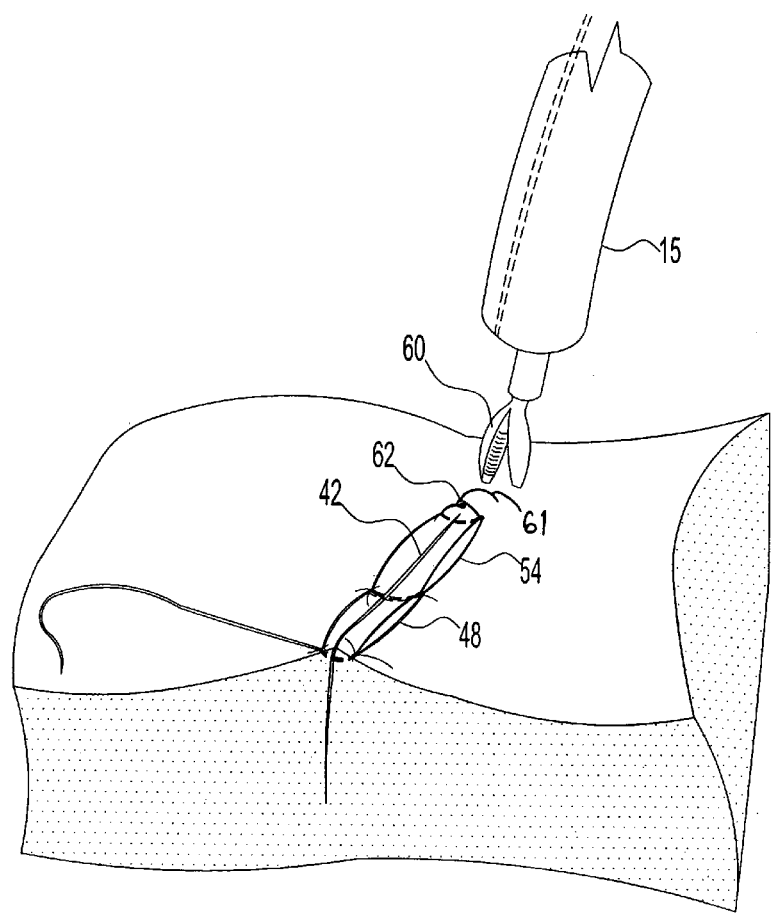

As depicted in FIG. 4M, one end of thread 18 may be pulled to tighten the loops 48, 54, 56 so that they extend end-to-end alongside the incision 42. A spanning portion 58 of the thread 18 generally extends across the incision 42 proximate the end of each loop. As depicted in FIG. 4N, the tubular member 12 may be fully retracted into the endoscope 15 since only thread 18 is exposed. Cutter 60 may then be employed out of a working channel of the endoscope 15 to cut the thread 18, freeing the endoscope from the suture (48, 54, 56). When the suture thread is appropriately pulled and tightened, the spanning sections 58 across the suture are shortened, closing the incision 42. The grasper 60 may be used to form closure knot 62 as shown in FIG. 4O, utilizing the final loop 56. A longer suture might require additional loops and additional spanning portions of the suture thread 18. Additional loops would be formed by repeating the back and forth sequence wherein the next sequential loop is passed through the previous loop in the overall suture.

Figure 5:
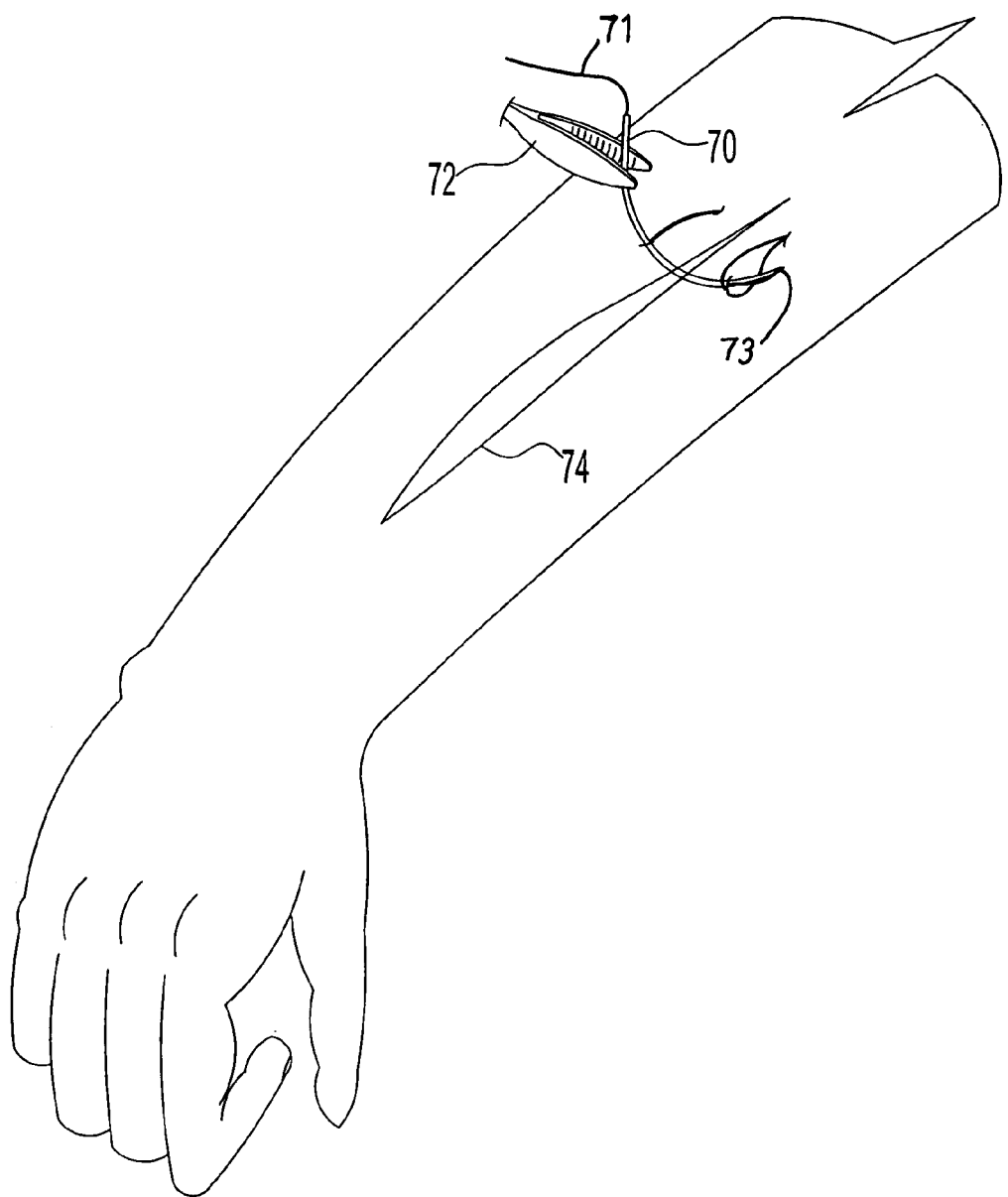
FIG. 5 is a schematic perspective view of an alternative use for the suturing needle of FIG. 3 in accordance with the principles of the present invention.

FIG. 5 illustrates a related suturing procedure wherein a needle 70 having a portion of the suture thread 71 passing therethrough and out the distal end 73 of the needle is utilized by itself, rather than with an endoscope. The needle 70 might be grasped with a forceps 72 or other suitable device and used to manually stitch a wound or incision 74 with a back-and-forth loop-through-loop methodology described hereinabove. Thus, the disclosed methodology may be used to close wounds or incisions 74 in external tissues such as skin, as well, as shown in FIG. 5.

Figure 6:
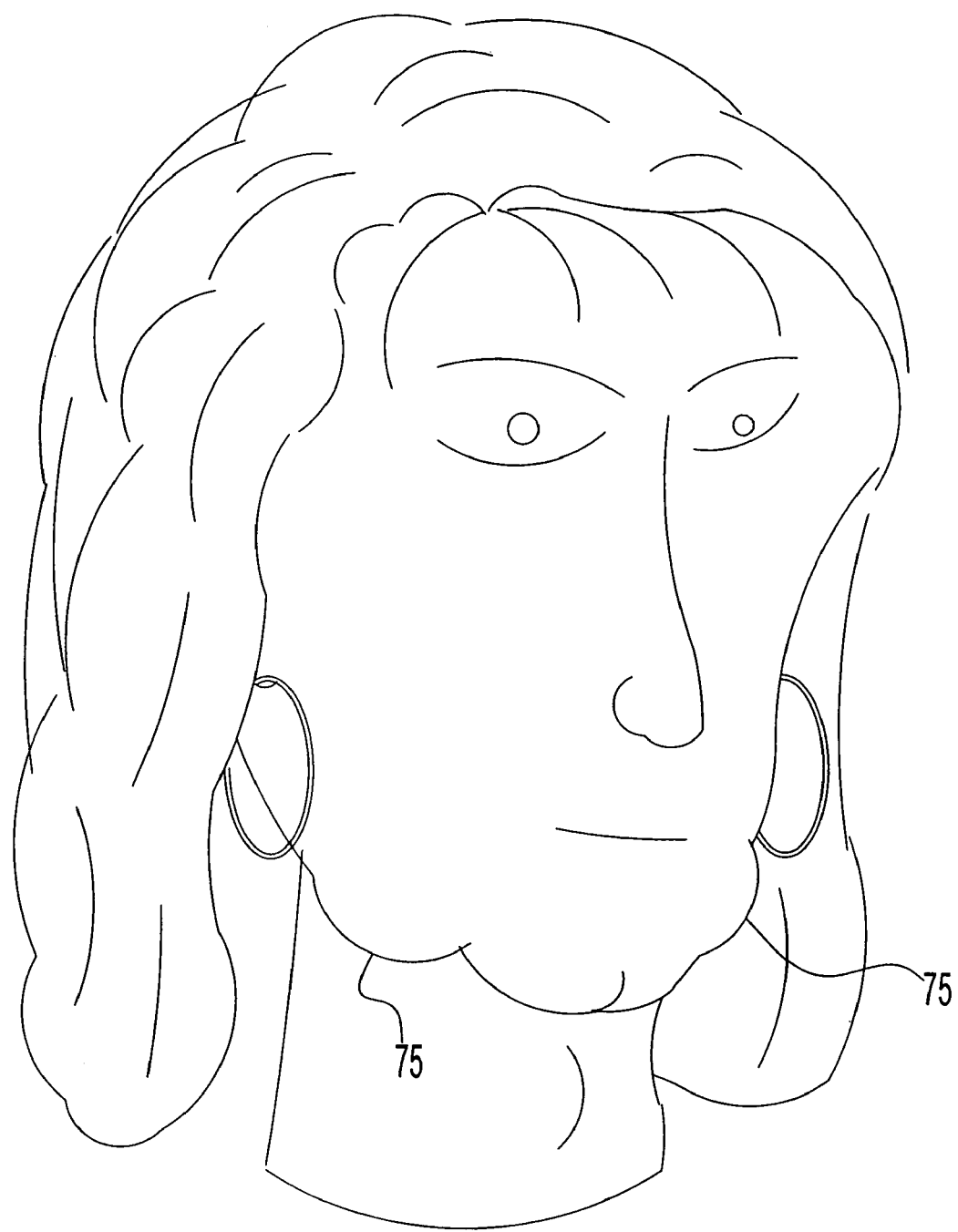
FIG. 6 is a schematic perspective view of a patient having a condition, which may be treated utilizing a suturing needle in accordance with the present invention.
Figure 6A:
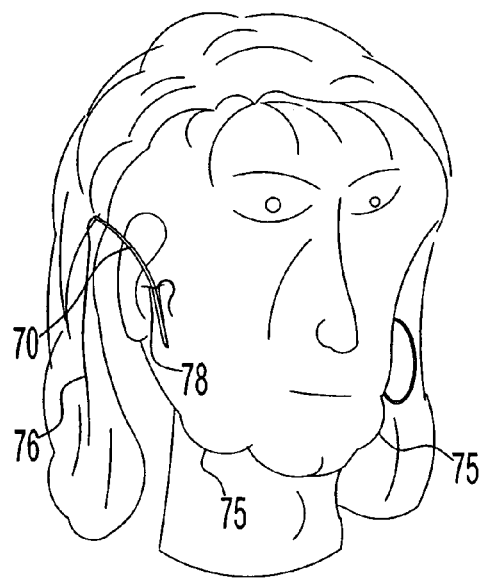
FIGS. 6A-6H are sequential schematic perspective views of the patient with the condition illustrated in FIG. 6, showing successive steps in a treatment of the condition in accordance with the present invention.
Figure 6B:
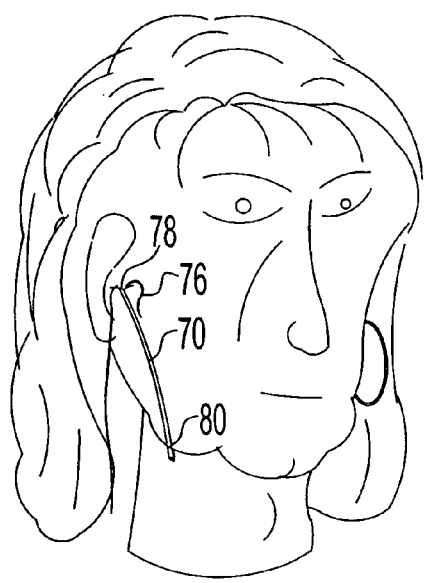
Figure 6C:
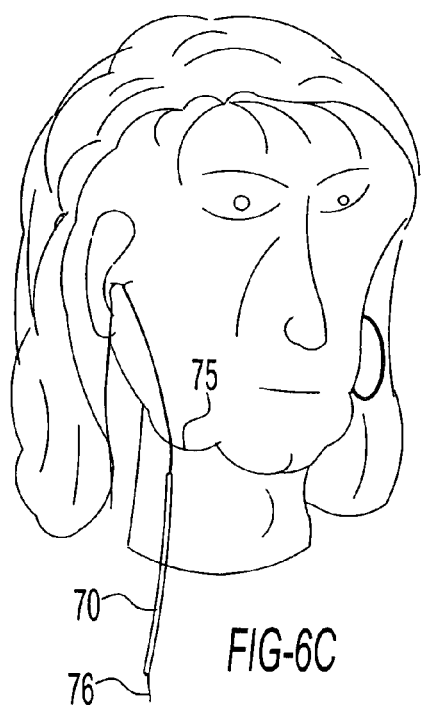
Figure 6D:
Figure 6E:
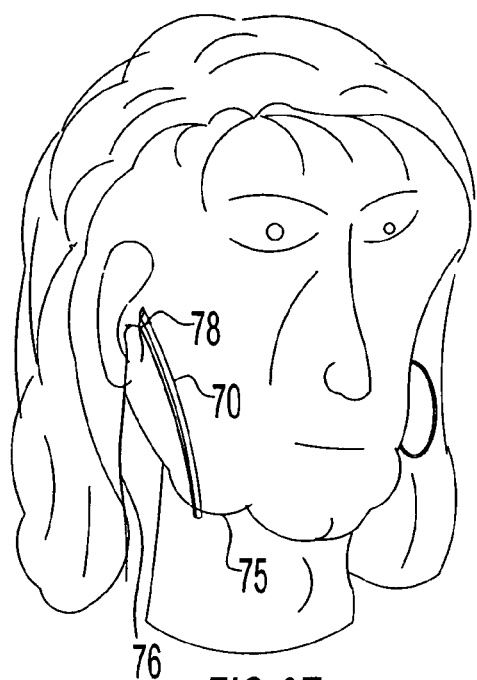
Figure 6F:
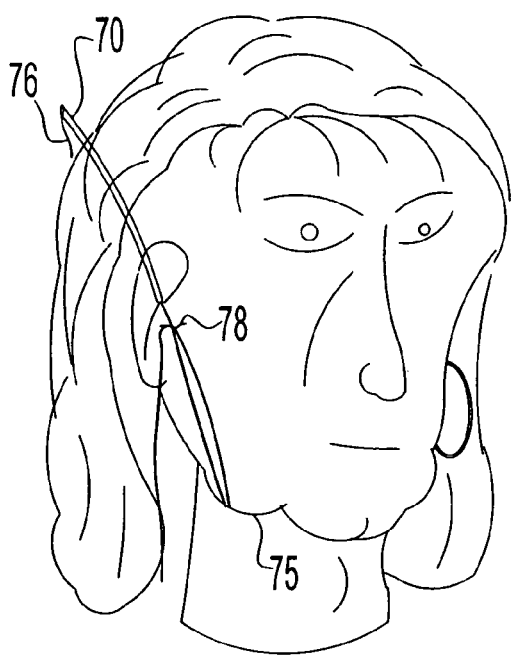

FIG. 6 is a frontal view of a patient with jaw-line fat pads 75 and 75' intended for cosmetic surgical repair. FIG. 6A additionally illustrates a hollow suture needle 70 with a suture thread 76 longitudinally traversing the needle. Suture needle 70 is inserted through an incision 78 made in the frontal area of the ear inside the patient's hairline. Per FIG. 6B, suture needle 70 is inserted through incision 78 in the direction of a fat pad 75. The needle 70 is pushed towards the fat pad 75, until it emerges at a first exit point 80. As shown in FIG. 6C, needle 70 is withdrawn from the target tissue. As shown in FIG. 6D, needle 70 is reintroduced into fat pad 75 through the first exit point 80 and directed back towards incision 78. In FIG. 6E, needle 70 traverses a path proximate and substantially parallel to the first path of the suture thread 76, but not coincident with it. In FIG. 6F needle 70 exits through incision 78.

Figure 6G:
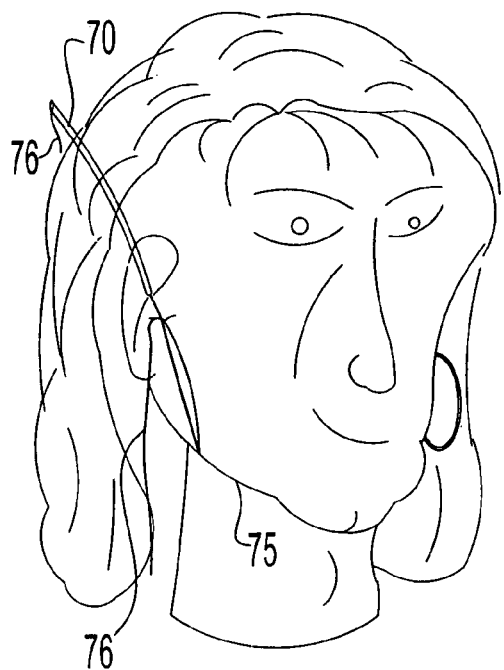
Figure 6H:

In FIG. 6G the two ends of suture 76 are synched together, lifting fat pad 75. In FIG. 6H a suture knot 82 is formed securing the face lift on the first side. Later, the incision 78 is closed by means of a suture applied in a state of the art fashion. The same procedure is repeated on the contralateral side, and the lower face lift is thus completed.

In a preferred embodiment of endoscopic suturing device 10, needle 16 is integrally formed with push rod 14 as an elongate flexible tubular member provided at the distal end with a temperature-responsive shape memory configuration. Suture thread 18 extends through the entire length of the push rod and needle. Thus, thread 18 extends a distance out of the proximal end of the device 10 and out of the endoscope 15 when in operation, and out of the distal end of the needle 16. In addition the opening 46 wherefrom the thread 18 exits the needle 16 distally may be located at a position that is removed from the tip 21 and located in the inner aspect of the curve, as depicted at 46' in FIG. 1. This configuration ensures that when the needle 16 enters the tissue 40, that the needle will not sever the thread 18. In some applications, the opening 46 may be located on the outside of the curved portion of needle 18, as indicated at 46" in FIG. 1.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An endoscopic suturing assembly for use with an endoscope, comprising:
   a suture needle having an elongate flexible shaft and a longitudinal passageway therethrough, said passageway extending substantially along the length of said needle to an opening in a distal end portion of said needle, at least a distal end portion of said needle being made of a shape-memory material tending to form said distal end portion of said needle from a first configuration to a second configuration;
   a suture thread slidably extending through said passageway and out of said needle through said opening;
   an elongate tubular member for housing said needle; and
   a heating collar provided at a distal end of said tubular member, for changing said needle from said first configuration to said second configuration
   said needle being slidably positioned inside said tubular member for enabling motion of said needle alternately in a distal and a proximal direction.

2. A suturing assembly comprising:
   a tubular member configured for insertion through a working channel of an endoscope;
   a needle member having (a) an integral or inseparable elongate shaft insertable through said tubular member so as to extend longitudinally along at least a substantial portion of said tubular member, (b) a pointed distal tip, (c) a distal end portion made of a shape memory material, so that said distal end portion changes from a first configuration to a second configuration upon an ejection from said tubular member, (d) a hollow passageway extending longitudinally through said needle member from a proximal end of said shaft to an opening along said distal end portion of said needle member;

a heating collar provided at a distal end of said tubular member; for changing said needle from the first configuration to the second configuration and a suture thread slidably extending from said proximal end of said shaft through said passageway and out of said needle member through said opening.

3. A suturing assembly comprising:

an elongate tubular member;

a suture needle made of shape memory material and slidably disposed in part within said tubular member, said needle having a shaft and a pointed distal tip, a hollow passageway extending longitudinally through said shaft to an opening along a distal end portion of said needle;

a heating collar provided at a distal end of said tubular member; for changing said needle from the first configuration inside said tubular member to the second configuration outside said tubular member and a suture thread extending through said passageway and out of said needle through said opening, a proximal end of said suture thread extending out of a proximal end of said shaft of said needle.

4. The suturing assembly set forth in claim 3 wherein said passageway extends substantially along the length of said needle.

5. The suturing assembly set forth in claim 3 wherein said needle has a cross-section taken from the group consisting of triangular, rectangular or rounded.

\* \* \* \* \*